US009572908B2

(12) United States Patent
Bianco-Peled et al.

(10) Patent No.: US 9,572,908 B2
(45) Date of Patent: Feb. 21, 2017

(54) MANUFACTURING AND APPLICATIONS OF ADHESIVE MATERIALS

(71) Applicant: TECHNION RESEARCH & DEVELOPMENT FOUNDATION LTD., Haifa (IL)

(72) Inventors: Havazelet Bianco-Peled, Haifa (IL); Ronit Biton, Herzlia (IL)

(73) Assignee: Technion Research & Development Foundation Ltd., Haifa (IL)

( * ) Notice: Subject to any disclaimer, the term of this patent is extended or adjusted under 35 U.S.C. 154(b) by 345 days.

(21) Appl. No.: 14/479,798

(22) Filed: Sep. 8, 2014

(65) Prior Publication Data

US 2014/0377208 A1      Dec. 25, 2014

Related U.S. Application Data

(62) Division of application No. 11/885,555, filed as application No. PCT/IL2006/000289 on Mar. 2, 2006, now Pat. No. 8,829,075.

(60) Provisional application No. 60/657,413, filed on Mar. 2, 2005.

(51) Int. Cl.
| | |
|---|---|
| A61K 6/00 | (2006.01) |
| A61L 24/08 | (2006.01) |
| A61L 24/00 | (2006.01) |
| C08L 5/04 | (2006.01) |
| C08L 101/00 | (2006.01) |
| C09J 105/04 | (2006.01) |

(52) U.S. Cl.
CPC ............ *A61L 24/08* (2013.01); *A61L 24/0005* (2013.01); *A61L 24/0073* (2013.01); *C08L 5/04* (2013.01); *C08L 101/00* (2013.01); *C09J 105/04* (2013.01)

(58) Field of Classification Search
CPC ... A61L 24/0005; C09J 105/04; C08L 101/00; C08L 5/04
USPC ........................................................ 523/118
See application file for complete search history.

(56) References Cited

U.S. PATENT DOCUMENTS

| | | | |
|---|---|---|---|
| 2,884,389 | A | 4/1959 | Corwin et al. |
| 3,802,897 | A | 4/1974 | Voigt |
| 4,057,588 | A | 11/1977 | Zengel et al. |
| 5,520,727 | A | 5/1996 | Vreeland et al. |
| 6,146,497 | A | 11/2000 | Nguyen |
| 6,544,503 | B1 | 4/2003 | Vanderhoff et al. |
| 7,365,190 | B2 | 4/2008 | Couture et al. |
| 2002/0010150 | A1 | 1/2002 | Cortese et al. |
| 2002/0086175 | A1 | 7/2002 | Parg et al. |
| 2004/0018241 | A1 | 1/2004 | Houze et al. |
| 2006/0269480 | A1 | 11/2006 | Amir et al. |

FOREIGN PATENT DOCUMENTS

| | | |
|---|---|---|
| FR | 804128 | 10/1936 |
| JP | 2002-509171 A | 3/2002 |
| WO | 2006/092798 | 9/2006 |

OTHER PUBLICATIONS

Examination Report Dated Jul. 21, 2009 From the Intellectual Property Office of New Zealand Re.: Application No. 562002.
International Search Report Dated Jun. 18, 2007 From the International Searching Authority Re.: Application No. PCT/IL2006/000289.
Written Opinion Dated Jun. 18, 2007 From the International Searching Authority Re.: Application No. PCT/IL2006/000289.
Examiner's Report Dated Aug. 26, 2010 From the Australian Government, IP Australia Re. Application No. 2006219568.
Response Dated Aug. 22, 2011 to Examiner's Report of Aug. 26, 2010 From the Australian Government, IP Australia Re. Application No. 2006219568.
Response Dated Aug. 24, 2011 to Examiner's Report Dated Aug. 26, 2010 From the Australian Government, IP Australia Re. Application No. 2006219568.
Office Action Dated Sep. 20, 2011 From the Israel Patent Office Re. Application No. 185658 and Its Translation Into English.
Response Dated Mar. 11, 2010 to Examination Report of Jul. 21, 2009 From the Intellectual Property Office of New Zealand Re.: Application No. 562002.
Berglin et al. "Enzymatic Cross-Linking of a Phenolic Polymer Extracted From the Marine Alga Fucus Serratus", Biomacromolecules, 5: 2376-2383, 2004.
Draget et al. "Alginate-Based Soli Media for Plant Tissue Culture", Applied Microbiology and Biotechnology, 31: 79-83, 1989.
Dumitriu "Polysaccharides as Biomaterials", Polymeric Biomaterials, Chap.I: 1-61, 2002.
Ennker et al. "Formaldehyde-Free Collagen Glue in Experimental Lung Gluing", Annals ofThoracic Surgeons, 57: 1622-1627, 1994.
Huang et al. "Synthesis and Characterization of Self-Assembling Block Copolymers Containing Adhesive Moieties", Polymer Preprints, 42(2): 147-148, 2001.
Ishihara et al. "Photocrosslinkable Chitosan: An Effectice Adhesive With Surgical Applications", International Congress Series, 1223: 251-257,2001.

(Continued)

*Primary Examiner* — Hannah Pak
(74) *Attorney, Agent, or Firm* — Roach Brown McCarthy & Gruber, P.C.; Kevin D. McCarthy

(57) ABSTRACT

A novel method of manufacturing and applications of a composition of matter comprising of a cross-linked form of a polysaccharide, at least one cross-linking agent comprised of divalent ions for effecting said cross-linked form of said polysaccharide, and at least one synthetically prepared phloroglucinol compound selected from the group comprising of phloroglucinol, a derivative of phloroglucinol, and a polymer synthetically prepared from phloroglucinol or a derivative of phloroglucinol, as an adhesive in procedures for reattaching or repairing body parts or components thereof, such as tissue, of (human or animal) subjects, especially under wet conditions, for example, involving adhesion of wet surfaces.

25 Claims, 5 Drawing Sheets

(56) References Cited

OTHER PUBLICATIONS

Ismaili et al. "Phloroglucinol: Novel Synthesis and Role of the Magnesium Cation on Its Binding With Human Serum Albumin (HSA) Using a Biochromatographic Approach Based on Langmuir Isotherms", Journal of Pharmaceutical and Biomedical Analysis, 32: 549-553, 2003.
Lee et al. "Synthesis and Gelation of DOPA-Modified Poly(Ethylene Glycol) Hydrogels", Biomacromolecules, 3: 1038-1047, 2002.
Li et al. "Novel Visible-Light-Induced Photocurable Tissue Adhesive Composed of Multiply Styrene-Derivatized Gelatin and Poly(Ethylene Glycol) Diacrylate", Journal of Biomedical Materials Research Part B: Applied Biomaterials, 66B: 439-446, 2003.
Lipatova "Medical Polymer Adhesives", Advances in Polymer Science, 79: 65-93, 1986.
Lucas et al. "Extra-Organismic Adhesive Proteins", Biopolymers, 8: 359-382, 2001.
Manabe et al. "In Situ-Formed, Tissue-Adhesive Co-Gel Composed of Styrenated Gelatin and Styrenated Antibody: Potential Use for Local Anti-Cytokine Antibody Therapy on Surgically Resected Tisues", Biomaterials, 25: 5867-5873, 2004.
Masuda et al. "Photocured, Styrenated Gelatin-Based Microspheres for De Novo Adipogenesis Through Core lase of Basic Fibroblast Growth Factor, Insulin, and Insulin-Like Growth Factor I", Tissue Engineering, 1 0(3/4): 523-536, 2004.
McDermott et al. "Mechanical Properties of Biomimetic Tissue Ashesive Based on the Microbial Transglutaminase-Catalyzed Cross linking of Gelatin", Biomacromolecules, 5: 1270-1279, 2004.

Mo et al. "Soft Tissue Adhesive Composed of Modified Gelatin and Polysaccharides", Journal of Biomaterials Science, Polymer Edition, 11(4): 341-351, 2000.
Reece et al. "A Prospectus on Tissue Adhesives", The American Journal of Surgery, 182: 40S-44S, 2001.
Singer et al. "A Review of the Literature on Octylcyanoacrylate Tissue Adhesive", The American Journal of Surgery, 187: 238-248, 2004.
Vreeland et al. "Polyphenols and Oxidases in Substratum Adhesion by Marine Algae and Mussels", Journal of Phycology, 34: 1-8, 1998.
Waite "Nature's Underwater Adhesive Specialist", International Journal of Adhesion and Adhesives, 7(1): 9-14, Jan. 1987.
Webster et al. "Adhesives for Medical Applications", Polymeric Biomaterials, Chap.26: 703-737, 2002.
White et al. "The Use of a Novel Tissue Sealant as a Hemostatic Adjunct in Cardiac Surgery", Heart Surgery Forum, 3(1): 56-61, 2000.
Yamamoto et al. "Synthesis and Wettability Characteristics of Model Adhesive Protein Sequences Inspired by a Marine Mussel", Biomacromolecules, 1: 543-551, 2000.
Yu et al. "Synthetic Polypeptide Mimics of Marine Adhesives", Macromolecules, 31:4739-4745, 1998.
International Preliminary Report on Patentability Dated Jan. 14, 2008 From the International Preliminary Examining Authority Re.: Application No. PCT/IL2006/000289.
International Preliminary Report on Patentability Dated Sep. 20, 2007 From the International Bureau of WIPO Re.: Application No. PCT/IL2006/000289.
Communication Pursuant to Article 94(3) EPC Dated Nov. 3, 2008 From the European Patent Office Re.: Application No. 06711271.4.
Communication Pursuant to Article 94(3) EPC Dated Jun. 26, 2009 From the European Patent Office Re.: Application No. 06711271.4.

Phloroglucinol (1,3,5-trihydroxybenzene)

alpha-L-glucuronic acid (G)

beta-D-mannuronic acid (M)

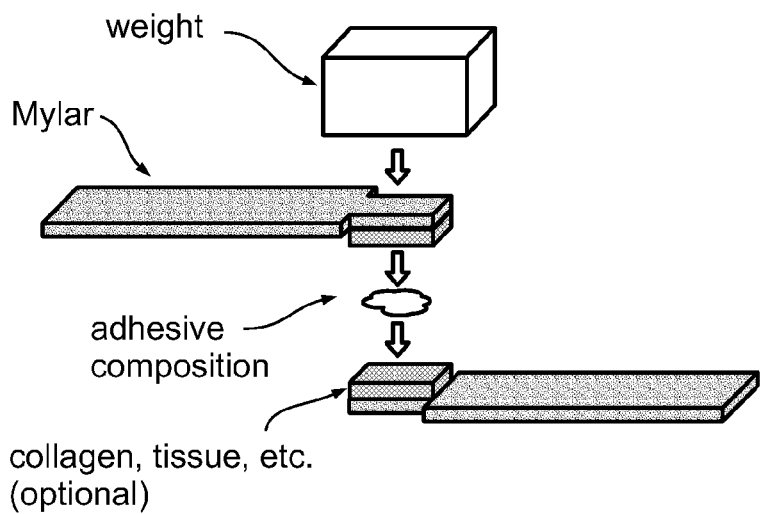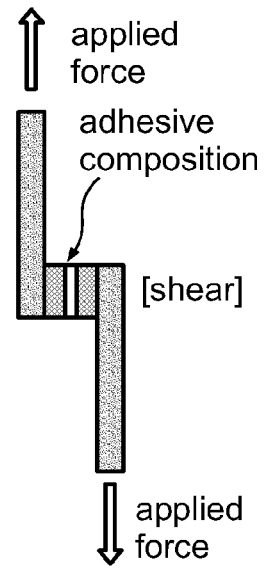
Fig. 4a
Fig. 4b
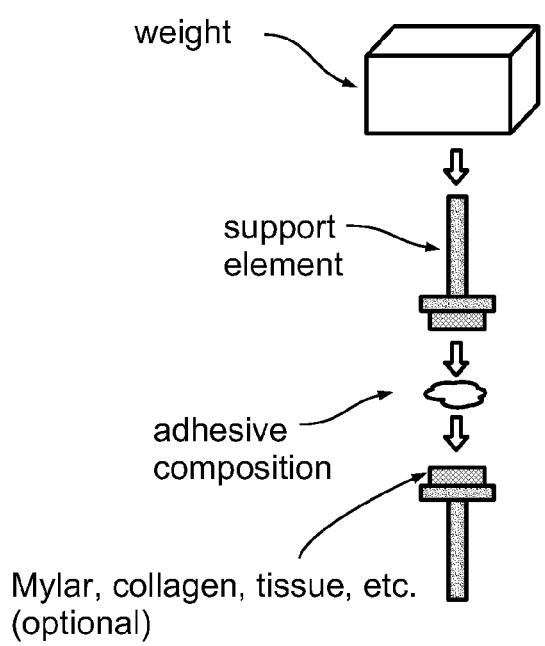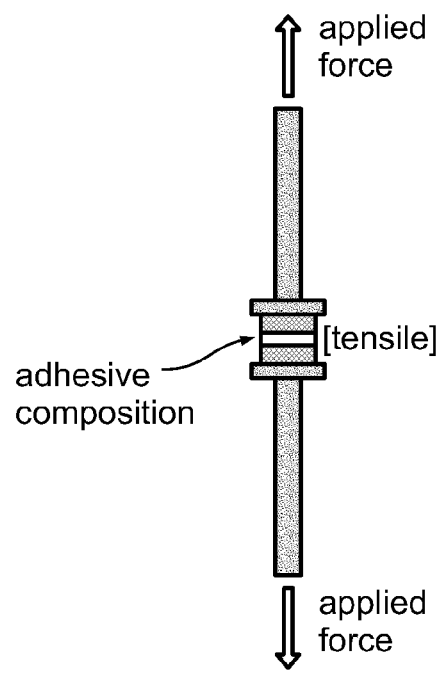
Fig. 4c
Fig. 4d

MANUFACTURING AND APPLICATIONS OF ADHESIVE MATERIALS

RELATED APPLICATIONS

This application is a Divisional Application of U.S. patent application Ser. No. 11/885,555 that is a National Phase of PCT Patent Application No. PCT/Th2006/000289 having International Filing Date of Mar. 2, 2006, which claims the benefit of U.S. Provisional Patent Application No. 60/657,413 filed on Mar. 2, 2005. The contents of the above applications are all incorporated herein by reference.

FIELD AND BACKGROUND OF THE INVENTION

The present invention relates to the field of adhesive materials, and more particularly, to a novel composition-of-matter, a method of manufacturing thereof, and applications thereof as an adhesive, in a wide variety of different fields, and in particular, in the health care fields of medicine, dentistry, and veterinary science. The present invention is especially applicable for use by health care providers, such as medical, dental, and veterinary, surgeons, in procedures for reattaching or repairing body parts or components thereof, such as tissue, of (human or animal) subjects, especially under wet conditions, for example, involving adhesion of wet surfaces. The composition-of-matter of the present invention, being functional and usable as an adhesive, may also be functional and usable as a sealant or sealing agent, for sealing or closing an opening in a (dry or wet) surface.

Herein, for the purpose of clarity and consistency, it is to be fully understood that the term 'adhesive' is synonymous with the term 'glue', whereby each refers to a material or substance which exhibits adhesive properties, characteristics, and behavior. Accordingly, herein, an adhesive synonymously and equivalently refers to a glue, and use of the term adhesive is meant to generally encompass either such term.

In the health care fields of medicine, dentistry, and veterinary science, there are many procedures which are based on, or at least involve, reattaching or repairing body parts or components thereof, such as tissue, particularly, of a wound, for example, either as part of, or immediately following, performing surgery on a (human or animal) subject or treating a subject for trauma. Currently practiced tissue reattachment or repair procedures are ordinarily based on the use of sutures, staples, or/and wires. Although such procedures are well established and widely used, their applications often involve discomfort or/and pain to subjects. Moreover, the use of sutures for closing a wound typically results in the presence of unaesthetic remnant small openings in the skin. These limitations have led to the use of different materials, in particular, adhesives (glues), in medical procedures for reattaching or repairing tissue [1].

By using an adhesive in a tissue reattachment or repair procedure, typically, the adhesive needs to be applied onto a wet tissue surface, in particular, wetted by any combination of liquids, such as blood, water, and medicinal liquids, such as antiseptic or/and antibiotic liquids. The primary function of a 'tissue' adhesive is for binding and adhering tissues to each. As a direct consequence of binding and adhering tissues to each, the tissue adhesive performs a variety of secondary functions, in particular, stopping bleeding, sealing of leaks, and facilitating healing processes.

There are currently several types of commercially available tissue adhesives, made from synthetic or/and naturally existing components, in which these functions are performed, via in situ generation of a three-dimensional (3-D) polymeric network that is bonded to the tissue [2]. Cyanoacrylates [3], polyurethanes [4], gelatin based adhesives [2], fibrin based adhesives [1], and collagen based adhesives [5], are the most familiar commercially available tissue adhesives. The most widely used synthetic adhesives are cyanoacrylates, also known as 'super glues'. They are applied as liquid monomers that polymerize on contact with tissue surfaces in an exothermic reaction creating a strong, yet flexible, film that bonds tissues of oppositely facing wound edges [3]. However, reported side affects, such as inflammatory response, delayed healing, necrosis, or/and thrombosis, limit their use as adhesives for internal organs [1]. Gelatin based adhesives form a network via crosslinking by resorcinol and formaldehyde. As with the cyanoacrylates, gelatin based adhesives are associated with toxicity issues [2]. Recently, there has been much effort to develop less toxic adhesives by using alternative materials, crosslinking chemistries, or controllable polymerization reactions, such as photo-initiated polymerization [6-12]. To date, none of these alternatives is commercially available.

The success of synthetic adhesives in a wet environment is limited, and typically requires carefully cleaned surfaces, which often must also be chemically treated and/or partially dried [13]. On the contrary, most adhesion events in nature occur under water. Many marine sessile organisms, such as mussels, barnacles, and tube worms, effectively stick to almost any wet surface [14]. Although a natural adhesive, such as 'mussel glue', made from naturally existing adhesive substances, in particular, proteins and polypeptides, obtained from these organisms, has been claimed to be suitable for medical applications, including, for example, during wet conditions, it is clear that commercial production of such a mussel glue is currently not practical, since, for example, extraction of 1 kg of the naturally existing adhesive raw materials (proteins and polypeptides) would require processing five to ten million mussels [1].

Another, yet equally effective natural adhesion mechanism exists in red and brown algae, which produce phenolic compounds that exhibit adhesive properties, characteristics, and behavior, and extraordinarily high cohesive strengths. These adhesive phenolic compounds bind non-specifically to both hydrophobic and hydrophilic surfaces in aqueous conditions [15]. Vreeland et al. [16] postulated that initial substratum adhesion by zygotes of the brown alga *Fucus gardenri* involves the secretion of polyphenols. Later on, these polyphenols are activated by a vanadate peroxidase type of enzyme catalyst for enabling cross-linking of polyphenols to extra cellular carbohydrate fibers, eventually leading to formation of an algal adhesive.

Vreeland, et al. [17] disclose various formulations of a water-resistant, aqueous, phenolic adhesive or glue derived from algal raw materials. The phenolic component of the disclosed adhesives is an algal phloroglucinol-based polyphenolic compound, containing from about 2 to 500,000 phloroglucinol (1,3,5-trihydroxybenzene) units, wherein the phloroglucinol units are joined by carbon-carbon bonds or by ether linkages. The algal derived adhesive polyphenolic compounds are preferably activated with an enzyme catalyst, such as vanadate-requiring peroxidase, horse radish peroxidase, mushroom polyphenoloxidase, or other oxidoreductase, or, by addition of an oxidizing agent, such as sodium hypochlorite, hydrogen peroxide, urea hydrogen peroxide, sodium hypochlorite, periodic acid, nitric acid, potassium permanganate, or potassium dichromate. The activated polyphenolic compound may be cross-linked with various natural or synthetic macromolecules, such as carbohydrates (for example, alginate or fucoidans), proteins, or fibers.

Covalent cross-linking of phenols to a substrate is also possible. Recently, Berglin, et al. [18] studied the enzymatic cross-linking of a phenolic polymer extracted from the alga *Fucus serratus* using the quartz crystal microbalance with dissipation monitoring methodology (QCM-D). Their results show that addition of a vanadium-dependent haloperoxidase enzyme, in particular, bromoperoxidase (BPO), along with potassium bromide (KBr), and hydrogen peroxide ($H_2O_2$), to the phenolic polymer, caused a decrease in dissipation, indicating that a cross-linking process may have occurred. Although all four components were proven to be necessary, the cross-linking mechanism remained unclear. The work by Berglin et al. has demonstrated the potential feasibility of using algal phenolic polymers as a component in a tissue adhesive.

Algal derived natural adhesives, such as the algal phloroglucinol-based polyphenolic adhesives disclosed by Vreeland, et al. [15, 17], have the same limitation regarding feasible commercial production, as for the previously described marine organism derived natural adhesives, such as mussel glue. An enormous quantity of brown algae is required for extracting a significantly smaller quantity of the naturally existing adhesive raw material (polyphenols). Moreover, once a suitable quantity of the naturally existing adhesive raw material (polyphenols) is made available, producing a 'usable' final form of such an algal derived natural adhesive requires performing a relatively long sequence of various chemical and physical separation and purification processes and procedures, which further brings into question the commercial feasibility and applicability of such natural adhesives.

Instead of attempting to produce a commercially feasible quantity of a natural adhesive, from naturally existing adhesive raw materials, such as proteins, polypeptides, or polyphenols, requiring processing an enormous quantity of a marine or aquatic organism, followed by having to perform a relatively long sequence of various chemical and physical separation and purification processes and procedures, an alternative and more practical method is based on taking a 'biomimetic' approach, whereby polymeric analogs are synthesized from amino acids that were identified in naturally existing adhesive proteins [13]. Much effort has been made to synthesize random block copolymer biomimetic approximations of naturally existing adhesive proteins and polypeptides. These attempts include synthesis of sophisticated peptide sequences identified in adhesive proteins of mussels [19], co-polypeptides containing DOPA [13], DOPA-modified polyethyleneglycol hydrogels [20], and DOPA modified pluronics [21]. However, to date, adhesive strengths achieved for biomimetic adhesives, for example, mussle glue imitations, have not been sufficient to stimulate interest in large-scale industrial production. Moreover, biomimetic adhesives have rarely been applied and cured on test surfaces located under water [22].

Based on the above stated disadvantages of using sutures, staples, or/and wires, in currently practiced tissue reattachment or repair procedures, and the above described limitations associated with currently commercially available tissue adhesives made from synthetic or/and naturally existing components, and limitations associated with natural adhesive formulations made from marine or aquatic organisms, as well as limitations associated with biomimetic approximations of natural adhesives, there continues to be an on-going need for developing new adhesives (glues), particularly in the health care fields of medicine, dentistry, and veterinary science, for use by health care providers, such as medical, dental, and veterinary, surgeons, in procedures for reattaching or repairing body parts or components thereof, such as tissue, especially under wet conditions, for example, involving adhesion of wet surfaces.

There is thus a need for, and it would be highly advantageous to have, a novel composition-of-matter, a method of manufacturing thereof, and applications thereof as an adhesive. There is a particular need for such an invention which is safe and effective for use on (human or animal) subjects, and which is especially applicable in the health care fields of medicine, dentistry, and veterinary science, for use in procedures for reattaching or repairing body parts or components thereof, such as tissue, especially under wet conditions, for example, involving adhesion of wet surfaces. There is additional need for such an invention which is commercially feasible and applicable, which doesn't require processing an enormous quantity of a marine or aquatic organism, followed by having to perform a relatively long sequence of various chemical and physical separation and purification processes and procedures, for producing a usable final form of the inventive adhesive.

There is additional need for such an invention wherein the composition-of-matter, being functional and usable as an adhesive, may also be functional and usable as a sealant or sealing agent, for sealing or closing an opening in a (dry or wet) surface, for example, for preventing flow of a (liquid or/and gaseous) fluid through the sealed or closed portion of the surface. Moreover, there is a need for such an invention which is generally applicable in a wide variety of different fields, in addition to the health care fields.

SUMMARY OF THE INVENTION

The present invention relates to a novel composition-of-matter, a method of manufacturing thereof, and applications thereof as an adhesive, in a wide variety of different fields, and in particular, in the health care fields of medicine, dentistry, and veterinary science. The present invention is especially applicable for use by health care providers, such as medical, dental, and veterinary, surgeons, in procedures for reattaching or repairing body parts or components thereof, such as tissue, of (human or animal) subjects, especially under wet conditions, for example, involving adhesion of wet surfaces. The composition-of-matter of the present invention, being functional and usable as an adhesive, may also be functional and usable as a sealant or sealing agent, for sealing or closing an opening in a (dry or wet) surface, for example, for preventing flow of a (liquid or/and gaseous) fluid through the sealed or closed portion of the surface. Such a sealant or sealing agent can be used in a wide variety of applications, for example, for sealing or closing an opening in a (dry or wet) body part, or in a (dry or wet) surface of a medical device, of an aquarium, or of a wide variety of other objects or entities.

The composition-of-matter of the present invention includes a cross-linked form of a water miscible polymer, and at least one phloroglucinol type compound selected from the group consisting of: phloroglucinol, a derivative of phloroglucinol, and a polymer synthetically prepared from phloroglucinol or a derivative of phloroglucinol.

In the composition-of-matter, any number of the indicated phloroglucinol type compounds is in a monomeric form or/and in a (non-cross-linked or/and cross-linked) polymeric form. In general, the (non-cross-linked or/and cross-linked) polymeric form of any number of the indicated phloroglucinol type compounds may contain a plurality of from about 2 to about 500,000 monomer units of phloroglucinol, or of a derivative of phloroglucinol. The (non-cross-linked or/and cross-linked) polymeric form of any number of the phloroglucinol type compounds may be formed in situ from monomers, oligomers, or/and polymers. The polymeric form may be an oligomer, i.e., having a relatively low molecular weight or/and a relatively low number of monomer units, e.g., dimers, trimers, . . . , tetramers, . . . , etc. The polymeric form may have a 'geometrical' shape, form, or configuration, selected from the group consisting of linear, non-linear, branched or dendrimeric (e.g., branched polymers or dendrimers), star, polygonal, elliptical, and any combination thereof.

In an exemplary preferred embodiment of the present invention, the composition-of-matter is manufactured in a manner which results in the composition-of-matter including any number of the above described phloroglucinol type compounds optionally being in a monomeric form or/and in a cross-linked polymeric form. For obtaining such an exemplary preferred embodiment, cross-linking of the monomeric form, or/and cross-linking of the polymeric form, of the at least one phloroglucinol type compound is effected by, optionally, using at least one activating agent. More specifically, wherein the cross-linked polymeric form is obtained by, optionally, admixing at least one activating agent with the water miscible polymer and the at least one phloroglucinol type compound, for effecting cross-linking of the monomeric form or/and of the polymeric form.

Accordingly, in such an exemplary preferred embodiment, optionally, at least one activating agent is used in the manufacturing method for promoting reaction and possible cross-linking, or/and oxidation, or/and some other modification, of any of the phloroglucinol type compounds. Such activating agents are, for example, a haloperoxidase (HPO) enzyme, an oxidizer, a halogen salt, and combinations thereof.

In general, the water miscible polymer is essentially any type or kind of naturally existing polymer or synthetically prepared polymer which is miscible in water.

In an exemplary preferred embodiment of the present invention, the water miscible polymer is a naturally existing, or synthetically prepared, form of a carbohydrate (polysaccharide), such as alginic acid, or/and alginic acid itself. More preferably, the water miscible polymer is a naturally existing, or synthetically prepared, salt form of a carbohydrate (polysaccharide), such as a salt form of alginic acid, being an alginate. The alginic acid or the alginate polymer is composed of either beta-D-mannuronic acid (M) units, or the alpha-L-glucuronic acid (G) units, in a range of between about 25 percent and about 75 percent, wherein the corresponding M/G ratio is in a range of between about 0.3 and about 3. Exemplary salt forms of alginic acid are alkali metal salts of alginic acid, such as sodium alginate and potassium alginate. Preferably, the alkali metal salt of alginic acid, sodium alginate, is used for implementing the present invention. The water miscible polymer is in a cross-linked form. For an embodiment of the composition-of-matter of the present invention, wherein the water miscible polymer is an alginate, or alginic acid, preferably, the alginate, or the alginic acid, is cross-linked via interaction with divalent ions, for example, divalent calcium ions ($Ca^{+2}$) supplied, for example, by calcium chloride ($CaCl_2$), or by a combination of calcium carbonate ($CaCO_3$) and glucono-δ-lactone (GDL).

Thus, according to the present invention, there is provided a composition-of-matter comprising a cross-linked form of a water miscible polymer, and at least one phloroglucinol type compound selected from the group consisting of: phloroglucinol, a derivative of phloroglucinol, and a polymer synthetically prepared from phloroglucinol or a derivative of phloroglucinol.

According to further characteristics in preferred embodiments of the invention described below, the at least one phloroglucinol type compound is in a monomeric form.

According to further characteristics in preferred embodiments of the invention described below, the at least one phloroglucinol type compound is in a non-cross-linked polymeric form or/and in a cross-linked polymeric form.

According to further characteristics in preferred embodiments of the invention described below, the non-cross-linked polymeric form or/and said cross-linked polymeric form is an oligomer.

According to further characteristics in preferred embodiments of the invention described below, the cross-linked polymeric form is obtained by admixing at least one activating agent with said water miscible polymer and said at least one phloroglucinol type compound, for effecting said cross-linked polymeric form.

According to further characteristics in preferred embodiments of the invention described below, the at least one activating agent is selected from the group consisting of a haloperoxidase enzyme, an oxidizer, a halogen salt, and combinations thereof.

According to further characteristics in preferred embodiments of the invention described below, the at least one phloroglucinol type compound is phloroglucinol or a derivative of phloroglucinol represented by the general structure:

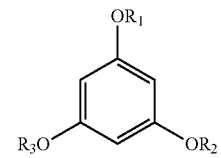

wherein $R_1$-$R_3$ are each independently selected from the group consisting of hydrogen, alkyl, cycloalkyl, and aryl.

According to further characteristics in preferred embodiments of the invention described below, the at least one phloroglucinol type compound is phloroglucinol.

According to further characteristics in preferred embodiments of the invention described below, the at least one phloroglucinol type compound is synthetically prepared.

According to further characteristics in preferred embodiments of the invention described below, the at least one phloroglucinol type compound is the polymer synthetically prepared from phloroglucinol or a derivative of phloroglucinol.

According to further characteristics in preferred embodiments of the invention described below, the synthetically prepared polymer contains a plurality of from about 2 to about 500,000 phloroglucinol monomer units.

According to further characteristics in preferred embodiments of the invention described below, the synthetically prepared polymer is an oligomer.

According to further characteristics in preferred embodiments of the invention described below, the synthetically prepared polymer is in a non-cross-linked form.

According to further characteristics in preferred embodiments of the invention described below, the synthetically prepared polymer is in a cross-linked form.

According to further characteristics in preferred embodiments of the invention described below, the cross-linked form is obtained by admixing at least one activating agent with the water miscible polymer and the at least one phloroglucinol type compound, for effecting cross-linking of the cross-linked form.

According to further characteristics in preferred embodiments of the invention described below, the at least one activating agent is selected from the group consisting of a haloperoxidase enzyme, an oxidizer, a halogen salt, and combinations thereof.

According to further characteristics in preferred embodiments of the invention described below, the haloperoxidase enzyme is selected from the group consisting of bromoperoxidase, potassium peroxidase, and combinations thereof.

According to further characteristics in preferred embodiments of the invention described below, the haloperoxidase enzyme is bromoperoxidase.

According to further characteristics in preferred embodiments of the invention described below, the oxidizer is a peroxide, a strong acid, potassium permanganate, potassium dichromate, and combinations thereof.

According to further characteristics in preferred embodiments of the invention described below, the oxidizer is a peroxide.

According to further characteristics in preferred embodiments of the invention described below, the peroxide is hydrogen peroxide.

According to further characteristics in preferred embodiments of the invention described below, the halogen salt is selected from the group consisting of potassium iodide, potassium bromide, potassium chloride, sodium iodide, sodium bromide, sodium chloride, and combinations thereof.

According to further characteristics in preferred embodiments of the invention described below, the halogen salt is selected from the group consisting of potassium iodide, potassium bromide, and combinations thereof.

According to further characteristics in preferred embodiments of the invention described below, the halogen salt is potassium iodide.

According to further characteristics in preferred embodiments of the invention described below, the halogen salt is potassium bromide.

According to further characteristics in preferred embodiments of the invention described below, the phloroglucinol type compound has a concentration in a range of between about 0.01 weight percent and about 10 weight percent, of the total weight of the composition-of-matter.

According to further characteristics in preferred embodiments of the invention described below, the phloroglucinol type compound has a concentration in a range of between about 0.1 weight percent and about 2 weight percent, of the total weight of the composition-of-matter.

According to further characteristics in preferred embodiments of the invention described below, the phloroglucinol type compound has a concentration in a range of between about 0.4 weight percent and about 1 weight percent, of the total weight of the composition-of-matter.

According to further characteristics in preferred embodiments of the invention described below, the water miscible polymer is a naturally existing, or synthetically prepared, form of a carbohydrate.

According to further characteristics in preferred embodiments of the invention described below, the carbohydrate is selected from the group consisting of a salt form of alginic acid, alginic acid, and a combination thereof.

According to further characteristics in preferred embodiments of the invention described below, the salt form of alginic acid or the alginic acid contains alpha-L-glucuronic acid (G) units in a range of between about 25 percent and about 75 percent.

According to further characteristics in preferred embodiments of the invention described below, the salt form of alginic acid or the alginic acid contains said alpha-L-glucuronic acid (G) units in a range of between about 50 percent and about 70 percent.

According to further characteristics in preferred embodiments of the invention described below, the carbohydrate is a salt form of alginic acid.

According to further characteristics in preferred embodiments of the invention described below, the salt form of alginic acid is an alkali metal salt of alginic acid selected from the group consisting of sodium alginate, potassium alginate, and a combination thereof.

According to further characteristics in preferred embodiments of the invention described below, the composition-of-matter further includes a cross-linking agent for effecting said cross-linked form of said water miscible polymer.

According to further characteristics in preferred embodiments of the invention described below, the cross-linking agent comprises divalent ions.

According to further characteristics in preferred embodiments of the invention described below, the divalent ions are selected from the group consisting of calcium ions, magnesium ions, strontium ions, barium ions, and a combination thereof.

According to further characteristics in preferred embodiments of the invention described below, the divalent ions are divalent calcium ions.

According to further characteristics in preferred embodiments of the invention described below, the cross-linked form of the water miscible polymer has a concentration in a range of between about 0.1 weight percent and about 10 weight percent, of the total weight of the composition-of-matter.

According to further characteristics in preferred embodiments of the invention described below, the cross-linked form of the water miscible polymer has a concentration in a range of between about 0.5 weight percent and about 5 weight percent, of the total weight of the composition-of-matter.

According to further characteristics in preferred embodiments of the invention described below, the cross-linked form of the water miscible polymer has a concentration in a range of between about 2 weight percent and about 3 weight percent, of the total weight of the composition-of-matter.

According to further characteristics in preferred embodiments of the invention described below, the composition-of-matter has an adhesive strength of at least about 5 kPa.

According to further characteristics in preferred embodiments of the invention described below, the composition-of-matter has an adhesive strength of at least about 35 kPa.

According to further characteristics in preferred embodiments of the invention described below, the composition-of-matter has an adhesive strength of at least about 100 kPa.

According to another aspect of the present invention, there is provided a method of manufacturing the composition-of-matter of the present invention, the method comprising: providing a water-miscible polymer, as described hereinabove; providing a cross-linking agent, as described hereinabove; providing the at least one phloroglucinol type compound, as described hereinabove; and mixing the water miscible polymer, the cross-linking agent and the at least one phloroglucinol type compound, thereby obtaining the composition-of-matter.

According to further characteristics in preferred embodiments of the invention described below, the at least one phloroglucinol type compound is in a monomeric form.

According to further characteristics in preferred embodiments of the invention described below, the at least one phloroglucinol type compound is in a non-cross-linked polymeric form or/and in a cross-linked polymeric form.

According to further characteristics in preferred embodiments of the invention described below, the non-cross-linked polymeric form or/and said cross-linked polymeric form is an oligomer.

According to further characteristics in preferred embodiments of the invention described below, the cross-linked polymeric form is obtained by admixing at least one activating agent with said water miscible polymer and said at least one phloroglucinol type compound, for effecting said cross-linked polymeric form.

According to further characteristics in preferred embodiments of the invention described below, the method additionally includes admixing with the water miscible polymer and the at least one phloroglucinol type compound at least one activating agent, as described hereinabove, for effecting cross-linking of the phloroglucinol type compound.

According to another aspect of the present invention, there is provided a use of the composition-of-matter of the present invention as an adhesive.

According to further characteristics in preferred embodiments of the invention described below, the adhesive is usable under dry or wet conditions.

According to further characteristics in preferred embodiments of the invention described below, the adhesive is usable under dry conditions, for adhering a first surface to a second surface, wherein each of the first surface and the second surface is dry.

According to further characteristics in preferred embodiments of the invention described below, the adhesive is usable under wet conditions, for adhering a first surface to a second surface, wherein at least one of the first surface and the second surface is wet.

According to further characteristics in preferred embodiments of the invention described below, at least one of the first surface and the second surface is a body part or a component thereof, of a human or animal subject.

According to further characteristics in preferred embodiments of the invention described below, the component is a tissue.

According to further characteristics in preferred embodiments of the invention described below, the adhesive is usable as a sealant or sealing agent, for sealing or closing an opening in a surface.

According to further characteristics in preferred embodiments of the invention described below, the sealing or closing takes place under dry or wet conditions.

According to further characteristics in preferred embodiments of the invention described below, the surface having the opening is a body part or a component thereof, of a human or animal subject.

According to further characteristics in preferred embodiments of the invention described below, the component is a tissue.

According to another aspect of the present invention, there is provided a method of adhering a first surface to a second surface, the method comprising applying an effective amount of the composition-of-matter of the present invention onto a designated area of the first surface, contacting the designated area with at least a portion of the second surface, and providing a sufficient period of time for the first surface to adhere to the second surface, thereby adhering the first surface to the second surface.

According to further characteristics in preferred embodiments of the invention described below, each of the first surface and the second surface is dry.

According to further characteristics in preferred embodiments of the invention described below, the method is performed under wet conditions, wherein at least one of the first surface and the second surface is wet.

According to further characteristics in preferred embodiments of the invention described below, at least one of the first surface and the second surface is a body part or a component thereof, of a human or animal subject.

According to further characteristics in preferred embodiments of the invention described below, the component is a tissue.

According to another aspect of the present invention, there is provided an article-of-manufacture comprising a packaging material and the composition-of-matter of the present invention, described hereinabove, being contained within the packaging material, the composition-of-matter being identified for use as an adhesive.

According to further characteristics in preferred embodiments of the invention described below, the adhesive is usable as a sealant or sealing agent, for sealing or closing an opening in a surface.

The present invention successfully overcomes disadvantages of using sutures, staples, or/and wires, in currently practiced tissue reattachment or repair procedures, and overcomes limitations associated with currently commercially available tissue adhesives made from synthetic or/and naturally existing components. The present invention also overcomes limitations associated with natural adhesive formulations made from marine or aquatic organisms, as well as overcoming limitations associated with biomimetic approximations of natural adhesives.

The present invention is safe and effective for use on (human or animal) subjects, and is especially applicable in the health care fields of medicine, dentistry, and veterinary science, for use by health care providers, such as medical, dental, and veterinary, surgeons, in procedures for reattaching or repairing body parts or components thereof, such as tissue, especially under wet conditions, for example, involving adhesion of wet surfaces. The present invention is commercially feasible and applicable, and doesn't require processing an enormous quantity of a marine or aquatic organism, followed by having to perform a relatively long sequence of various chemical and physical separation and purification processes and procedures, for producing a usable final form of the inventive adhesive. Additionally, the composition-of-matter of the present invention, being functional and usable as an adhesive, may also be functional and usable as a sealant or sealing agent, for sealing or closing an opening in a (dry or wet) surface, for example, for preventing flow of a (liquid or/and gaseous) fluid through the sealed or closed portion of the surface. Moreover, the present invention is generally applicable in a wide variety of different fields, in addition to the health care fields.

BRIEF DESCRIPTION OF THE DRAWINGS

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings:

FIGS. 4a and 4b are pictorial diagrams illustrating formation (FIG. 4a) of a typical 'sandwich' type of specimen as a shear type 'adhesive joint' (FIG. 4b) in a specimen holder, for performing the Shear Lap Test, for measuring shear type adhesive strength of selected formulations of the adhesive composition-of-matter of the present invention, under dry or wet conditions, as detailed in Examples 1-10, in accordance with the present invention;

FIGS. 4c and 4d are pictorial diagrams illustrating formation (FIG. 4c) of a typical 'sandwich' type of specimen as a tensile type 'adhesive joint' (FIG. 4d) in a specimen holder, for performing the Tensile Test, for measuring tensile type adhesive strength of selected formulations of the adhesive composition-of-matter of the present invention, under dry conditions, as detailed in Examples 11-14, in accordance with the present invention;

DESCRIPTION OF THE PREFERRED EMBODIMENTS

Figure 1:
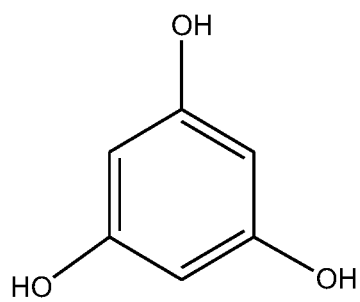
FIG. 1 presents a 2-D schematic illustration of the chemical structure of phloroglucinol (1,3,5-trihydroxybenzene), as a component included in exemplary preferred embodiments of the composition-of-matter of the present invention.

The present invention relates to a novel composition-of-matter, a method of manufacturing thereof, and applications thereof as an adhesive, in a wide variety of different fields, and in particular, in the health care fields of medicine, dentistry, and veterinary science. The present invention is especially applicable for use by health care providers, such as medical, dental, and veterinary, surgeons, in procedures for reattaching or repairing body parts or components thereof, such as tissue, of (human or animal) subjects, especially under wet conditions, for example, involving adhesion of wet surfaces. The composition-of-matter of the present invention, applied as an adhesive, may also function, and be usable, as a sealant or sealing agent, for sealing or closing an opening in a (dry or wet) surface, for example, for preventing flow of a (liquid or/and gaseous) fluid through the sealed or closed portion of the surface. Such a sealant or sealing agent can be used in a wide variety of applications, for example, for sealing or closing an opening in a (dry or wet) body part, or in a (dry or wet) surface of a medical device, of an aquarium, or of a wide variety of other objects or entities.

A main aspect of the present invention is provision of a composition-of-matter, as illustratively described hereinbelow, which includes a cross-linked form of a water miscible polymer, and at least one phloroglucinol type compound selected from the group consisting of: phloroglucinol, a derivative of phloroglucinol, and a polymer synthetically prepared from phloroglucinol or a derivative of phloroglucinol.

In the composition-of-matter, any number of the indicated phloroglucinol type compounds is in a monomeric form or/and in a (non-cross-linked or/and cross-linked) polymeric form. In general, the (non-cross-linked or/and cross-linked) polymeric form of any number of the indicated phloroglucinol type compounds may contain a plurality of from about 2 to about 500,000 monomer units of phloroglucinol, or of a derivative of phloroglucinol. The (non-cross-linked or/and cross-linked) polymeric form of any number of the phloroglucinol type compounds may be formed in situ from monomers, oligomers, or/and polymers. The polymeric form may be an oligomer, i.e., having a relatively low molecular weight or/and a relatively low number of monomer units, e.g., dimers, trimers, . . . , tetramers, . . . , etc. The polymeric form may have a 'geometrical' shape, form, or configuration, selected from the group consisting of linear, non-linear, branched or dendrimeric (e.g., branched polymers or dendrimers), star, polygonal, elliptical, and any combination thereof.

In an exemplary preferred embodiment of the present invention, the composition-of-matter is manufactured in a manner which results in the composition-of-matter including any number of the above described phloroglucinol type compounds optionally being in a monomeric form or/and in a cross-linked polymeric form. For obtaining such an exemplary preferred embodiment, cross-linking of the monomeric form, or/and cross-linking of the polymeric form, of the at least one phloroglucinol type compound is effected by, optionally, using at least one activating agent. More specifically, wherein the cross-linked polymeric form is obtained by, optionally, admixing at least one activating agent with the water miscible polymer and the at least one phloroglucinol type compound, for effecting cross-linking of the monomeric form or/and of the polymeric form.

Accordingly, in such an exemplary preferred embodiment, optionally, at least one activating agent is used in the manufacturing method for promoting reaction and possible cross-linking, or/and oxidation, or/and some other modification, of any of the phloroglucinol type compounds. Such activating agents are, for example, a haloperoxidase (HPO) enzyme, an oxidizer, a halogen salt, and combinations thereof.

In general, the water miscible polymer is essentially any type or kind of naturally existing polymer or synthetically prepared polymer which is miscible in water. In an exemplary preferred embodiment of the present invention, the water miscible polymer is a naturally existing, or synthetically prepared, form of a carbohydrate (polysaccharide), such as alginic acid, or/and alginic acid itself. More preferably, the water miscible polymer is a naturally existing, or synthetically prepared, salt form of a carbohydrate (polysaccharide), such as a salt form of alginic acid, being an alginate. The alginic acid or the alginate polymer contains either beta-D-mannuronic acid (M) units, or the alpha-L-glucuronic acid (G) units, in a range of between about 25 percent and about 75 percent, wherein the corresponding M/G ratio is in a range of between about 0.3 and about 3. Exemplary salt forms of alginic acid are alkali metal salts of alginic acid, such as sodium alginate and potassium alginate. Preferably, the alkali metal salt of alginic acid, sodium alginate, is used for implementing the present invention. The water miscible polymer is in a cross-linked form. For an embodiment of the composition-of-matter of the present invention, wherein the water miscible polymer is an alginate, or alginic acid, preferably, the alginate, or the alginic acid, is cross-linked via interaction with divalent ions, for example, divalent calcium ions ($Ca^{+2}$) supplied, for example, by calcium chloride ($CaCl_2$), or by a combination of calcium carbonate ($CaCO_3$) and glucono-δ-lactone (GDL).

Another main aspect of the present invention is provision of a method of manufacturing the composition-of-matter of the present invention, the method including the procedures of: providing a water-miscible polymer; providing a cross-linking agent for effecting the cross-linked form of the water-miscible polymer; providing the at least one phloroglucinol type compound; and mixing the water miscible polymer, the cross-linking agent and the at least one phloroglucinol type compound, thereby obtaining the composition-of-matter.

Another main aspect of the present invention is provision of a use of the composition-of-matter of the present invention as an adhesive. The adhesive composition is usable under dry or wet conditions, for adhering a first surface to a second surface, wherein at least one of the first surface and the second surface is dry, or, alternatively, wherein least one of the first surface and the second surface is wet. At least one of the first surface and the second surface is a body part or a component thereof (e.g., a tissue), of a human or animal subject. The adhesive may be functional and usable as a sealant or sealing agent, for sealing or closing an opening in a surface, for example, for preventing flow of a (liquid or/and gaseous) fluid through the sealed or closed portion of the surface. The sealing or closing may take place under dry or wet conditions. The surface having the opening which is sealed or closed may be a body part or a component thereof (e.g., a tissue), of a human or animal subject.

Another main aspect of the present invention is provision of a method of adhering a first surface to a second surface, the method including the procedure of applying an effective amount of the composition-of-matter of the present invention upon a designated area of the first surface, contacting the designated area with at least a portion of the second surface, and providing a sufficient period of time for the first surface to adhere to the second surface, thereby adhering the first surface to the second surface.

Another main aspect of the present invention is provision of an article-of-manufacture which includes (a) a packaging material, and (b) the composition-of-matter of the present invention being contained within the packaging material, wherein the composition-of-matter is identified for use as an adhesive. In the article-of-manufacture, the adhesive may be functional and usable as a sealant or sealing agent, for sealing or closing an opening in a surface, for example, for preventing flow of a (liquid or/and gaseous) fluid through the sealed or closed portion of the surface.

The present invention was arrived at mainly based on the knowledge that marine and aquatic organisms, such as mussels and algae, have natural inherently built-in adhesion mechanisms for highly effectively adhering to surfaces under dry or wet conditions. For example, as previously indicated in the Background [15, 16, 17], phenolic compounds naturally existing in algae exhibit adhesive properties, characteristics, and behavior, and extraordinarily high cohesive strengths. These adhesive phenolic compounds bind non-specifically to both hydrophobic and hydrophilic surfaces in aqueous conditions. For example, naturally existing phloroglucinol type compounds, in particular, algal phloroglucinol-based polyphenolic compounds, containing from about 2 to 500,000 phloroglucinol (1,3,5-trihydroxybenzene) monomeric units, have been used in formulations of natural adhesives or glues which exhibit adhesive strength under dry or wet conditions.

However, it is clearly understood that an enormous quantity of algae is required for extracting a significantly smaller quantity of the naturally existing adhesive raw material (polyphenols). Moreover, once a suitable quantity of the naturally existing adhesive raw material (polyphenols) is made available, producing a 'usable' final form of such an algal derived natural adhesive requires performing a relatively long sequence of various chemical and physical separation and purification processes and procedures, which brings into question the commercial feasibility and applicability of such natural adhesives.

Accordingly, the present inventors sought to overcome such significant limitations currently associated with large-scale commercial availability of naturally existing adhesive raw materials, such as polyphenols, and corresponding limitations associated with manufacturing usable forms of adhesives therefrom, while at the same time providing an adhesive composition-of-matter which is safe and effective for use on (human or animal) subjects, and which is especially applicable in the health care fields of medicine, dentistry, and veterinary science, for use in procedures for reattaching or repairing body parts or components thereof, such as tissue, under dry or wet conditions, for example, involving adhesion of wet surfaces.

It is to be understood that the present invention is not limited in its application to the details of the components of the disclosed composition-of-matter, or to the details of the order or sequence, and number, of procedures, steps, and sub-steps, or of the materials used, for implementing the disclosed method of manufacturing thereof, and applications thereof as an adhesive, set forth in the following description, accompanying drawings, or examples. For example, as illustratively described in the Examples section, hereinbelow, for exemplifying implementation of the present invention, adhesive strength, or tensile strength, of various formulations of the disclosed composition-of-matter was measured for a given formulation having been applied upon a designated area of different exemplary (dry or wet) surfaces, in particular, Mylar (plastic) strips, dry collagen, wet collagen, dry glass, dry polystyrene, or dry animal tissue.

Additionally, for example, the herein disclosed composition-of-matter is generally applicable for use as an adhesive, for adhering a first surface to a second surface, under dry or wet conditions, where, for example, the first surface or/and the second surface can be a body part or component thereof, such as tissue, of a (human or animal) subject. The adhesive may be functional and usable as a sealant or sealing agent, for sealing or closing an opening in a surface, for example, for preventing flow of a (liquid or/and gaseous) fluid through the sealed or closed portion of the surface. The sealing or closing may take place under dry or wet conditions. The surface having the opening which is sealed or closed may be a body part or a component thereof (e.g., a tissue), of a human or animal subject. Such a sealant or sealing agent can be used in a wide variety of applications, for example, for sealing or closing an opening in a (dry or wet) body part, or in a (dry or wet) surface of a medical device, of an aquarium, or of a wide variety of other objects or entities.

The present invention is especially applicable in the health care fields of medicine, dentistry, and veterinary science, for use by health care providers, such as medical, dental, and veterinary, surgeons, in procedures for reattaching or repairing body parts or components thereof, such as tissue, especially under wet conditions, for example, involving adhesion of wet surfaces. However, the present invention is also generally applicable in a wide variety of other fields. Accordingly, the present invention is capable of other embodiments and of being practiced or carried out in various ways. Although components, procedures, steps, sub-steps, and materials, similar or equivalent to those described herein can be used for practicing or testing the present invention, suitable components, procedures, steps, sub-steps, and materials, are described herein.

It is also to be understood that unless otherwise defined, all technical and scientific words, terms, or/and phrases, used herein throughout the present disclosure have either the identical or similar meaning as commonly understood by one of ordinary skill in the art to which this invention belongs. Phraseology, terminology, and, notation, employed herein throughout the present disclosure are for the purpose of description and should not be regarded as limiting. For example, the following description refers to the composition-of-matter as an adhesive, which, in addition to being functional and usable as an adhesive, may also be functional and usable as a sealant or sealing agent, for sealing or closing an opening in a (dry or wet) surface, in order to illustrate implementation of the present invention. As previously stated hereinabove, herein, for the purpose of clarity and consistency, it is to be fully understood that the term 'adhesive' is synonymous with the term 'glue', whereby each refers to a material or substance which exhibits adhesive properties, characteristics, and behavior. Accordingly, herein, an adhesive synonymously and equivalently refers to a glue, and use of the term adhesive is meant to generally encompass either such term. Moreover, all technical and scientific words, terms, or/and phrases, introduced, defined, described, or/and exemplified, in the above Background section, are equally or similarly applicable in the following illustrative description of the embodiments, examples, and appended claims, of the present invention. Additionally, as used herein, the term 'about' refers to ±10 percent of the associated value.

Components, procedures, steps, sub-steps, materials, operation, implementation, of exemplary preferred embodiments, alternative preferred embodiments, specific configurations, and, additional and optional aspects, characteristics, or features, thereof, of the composition-of-matter, method of manufacturing thereof, and applications thereof as an adhesive, according to the present invention, are better understood with reference to the following illustrative description and accompanying drawings.

In the following illustrative description of the present invention, included are main or principal components, procedures, steps, sub-steps, and materials, needed for sufficiently understanding proper 'enabling' utilization and implementation of the disclosed composition-of-matter, method of manufacturing thereof, and applications thereof as an adhesive. Accordingly, description of various possible required or/and optional preliminary, intermediate, minor, components, procedures, steps, sub-steps, or/and materials, of secondary importance with respect to enabling implementation of the invention, which are readily known by one of ordinary skill in the art, or/and which are available in the prior art and technical literature, are at most only briefly indicated herein.

Thus, a main aspect of the present invention is provision of a composition-of-matter which includes a cross-linked form of a water miscible polymer, and at least one phloroglucinol type compound selected from the group consisting of: phloroglucinol, a derivative of phloroglucinol, and a polymer synthetically prepared from phloroglucinol or a derivative of phloroglucinol.

As used herein, the phrase 'derivative of phloroglucinol', refers to a compound whose molecular structure is derived as a result of 'chemical modification' of the molecular structure of the phloroglucinol, such that a major portion of the phloroglucinol molecular structure remains unchanged or intact in the molecular structure of the derivative compound. The chemical modification of the molecular structure of the phloroglucinol takes place in an active manner, e.g., using synthetic organic chemistry methods and techniques, for forming an active type of derivative of the phloroglucinol. Alternatively, or additionally, the chemical modification of the molecular structure of the phloroglucinol takes place in a passive manner, i.e., by way of naturally occurring processes, mechanisms, or/and phenomena, for forming a passive type of derivative of the phloroglucinol. For example, a compound whose molecular structure is derived by (active or/and passive) addition of at least one substituent to, or/and by a change of at least one substituent from, the molecular structure of the phloroglucinol. For example, a compound whose molecular structure is derived by (active or/and passive) oxidation or hydrolysis of molecules of the phloroglucinol.

Accordingly, in general, preferred embodiments or formulations of the composition-of-matter of the present invention can be composed of any of numerous different combinations of a cross-linked form of a water miscible polymer, and at least one phloroglucinol type compound selected from the group consisting of: phloroglucinol, a derivative of phloroglucinol, and a polymer synthetically prepared from phloroglucinol or a derivative of phloroglucinol. Moreover, in general, preferred embodiments or formulations of the composition-of-matter of the present invention are not limited to having a specific number of any of the phloroglucinol group compounds.

More specifically, preferred embodiments or formulations of the composition-of-matter of the present invention can be composed of any of the following different combinations of a cross-linked form of a water miscible polymer and at least one phloroglucinol type compound:
 a cross-linked form of a water miscible polymer and phloroglucinol.
 a cross-linked form of a water miscible polymer and at least one derivative of phloroglucinol.
 a cross-linked form of a water miscible polymer and at least one polymer synthetically prepared from phloroglucinol or a derivative of phloroglucinol or a polymer (e.g., oligomer) thereof.

a cross-linked form of a water miscible polymer, phloroglucinol, and at least one derivative of phloroglucinol.

a cross-linked form of a water miscible polymer, phloroglucinol, and at least one polymer synthetically prepared from phloroglucinol or a derivative of phloroglucinol or a polymer (e.g., oligomer) thereof.

a cross-linked form of a water miscible polymer, phloroglucinol, at least one derivative of phloroglucinol, and at least one polymer synthetically prepared from phloroglucinol or a derivative of phloroglucinol or a polymer (e.g., oligomer) thereof.

The chemical structure of phloroglucinol (1,3,5-trihydroxybenzene) is shown in FIG. 1. Phloroglucinol, and derivatives thereof, for example, its trimethoxy derivative, (1,3,5-trimethoxybenzene), are known [23], as are methods of manufacturing such compounds.

Figure 2:
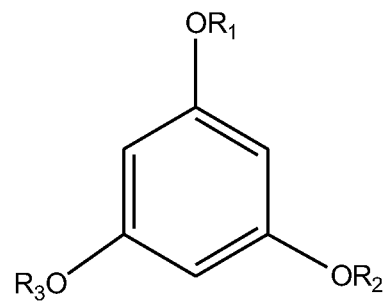
FIG. 2 presents a generalized 2-D schematic illustration of the chemical structure of phloroglucinol and derivatives thereof, as components included in exemplary preferred embodiments of the composition-of-matter of the present invention.

Phloroglucinol, and exemplary derivatives thereof, which are suitable for use in the context of the present invention, are represented by the general structure shown in FIG. 2, wherein $R_1$-$R_3$ are each independently selected from the group consisting of hydrogen, alkyl, cycloalkyl, and aryl.

As used herein, the term 'alkyl' refers to a saturated aliphatic hydrocarbon including straight chain and branched chain groups. Preferably, the alkyl group has 1 to 20 carbon atoms. Whenever a numerical range, for example, '1-20', is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms.

A 'cycloalkyl' group refers to an all-carbon monocyclic or fused ring (that is, rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane.

An 'aryl' group refers to an all-carbon monocyclic or fused-ring polycyclic (that is, rings which share adjacent pairs of carbon atoms) groups having a completely conjugated pi-electron system. Examples, without limitation, of aryl groups are phenyl, naphthalenyl and anthracenyl.

In the composition-of-matter of the present invention, any number of the at least one phloroglucinol type compound is in a monomeric form or/and in a (non-cross-linked or/and cross-linked) polymeric form. In general, the (non-cross-linked or/and cross-linked) polymeric form of any number of the indicated phloroglucinol type compounds may contain a plurality of from about 2 to about 500,000 monomer units of phloroglucinol, or of a derivative of phloroglucinol. The (non-cross-linked or/and cross-linked) polymeric form of any number of the phloroglucinol type compounds may be formed in situ from monomers, oligomers, or/and polymers. The polymeric form may be an oligomer, i.e., having a relatively low molecular weight or/and a relatively low number of monomer units, e.g., dimers, trimers, . . . , tetramers, . . . , etc. The polymeric form may have a 'geometrical' shape, form, or configuration, selected from the group consisting of linear, non-linear, branched or dendrimeric (e.g., branched polymers or dendrimers), star, polygonal, elliptical, and any combination thereof.

Such phloroglucinol type polymers can be synthetically prepared using polymerization procedures and techniques known in the art of organic synthesis, in general, and in the art of synthesizing polymers from aromatic monomers, in particular. Such procedures and techniques can be used for synthesizing, for example, various phloroglucinol type polyphenolic compounds, each containing a plurality of, for example, anywhere from about 2 to about 500,000, phloroglucinol monomer units, wherein the phloroglucinol monomer units are linked with carbon-carbon or ether bonds. The (non-cross-linked or/and cross-linked) polymeric form of any number of the phloroglucinol type compounds may be formed in situ from monomers, oligomers, or/and polymers.

Accordingly, in such an exemplary preferred embodiment, optionally, at least one activating agent is used in the manufacturing method for promoting reaction and possible cross-linking, or/and oxidation, or/and some other modification, of any of the phloroglucinol type compounds. Such activating agents are, for example, a haloperoxidase (HPO) enzyme, an oxidizer, a halogen salt, and combinations thereof.

Synthetically prepared phloroglucinol type polyphenolic compounds would 'mimic' the naturally existing phloroglucinol type compounds, in particular, algal phloroglucinol type polyphenolic compounds, containing various numbers of phloroglucinol monomer units, such as those illustratively described and used by Vreeland et al. [15, 17] in formulations of natural adhesives or glues which exhibit adhesive strength under dry or wet conditions.

Thus, preferred compounds which conform to the above illustratively described general structure, and which can be used for implementing the present invention, are phloroglucinol type compounds selected from the group consisting of: phloroglucinol, a derivative of phloroglucinol, and a polymer synthetically prepared from phloroglucinol or a derivative of phloroglucinol.

In general, the composition-of-matter of the present invention, so formed from manufacturing thereof, as described hereinbelow, includes any number of the above indicated phloroglucinol type compounds in a monomeric form or/and in a (non-cross-linked or/and cross-linked) polymeric form. More specifically, the composition-of-matter of the present invention, so formed from manufacturing thereof, as described hereinbelow, includes at least one phloroglucinol type compound selected from the group consisting of: phloroglucinol, a derivative of phloroglucinol, and a polymer synthetically prepared from phloroglucinol or a derivative of phloroglucinol, in a monomeric form or/and in a (non-cross-linked or/and cross-linked) polymeric form.

In general, in the composition-of-matter of the present invention, the at least one phloroglucinol type compound selected from the group consisting of: phloroglucinol, a derivative of phloroglucinol, and a polymer synthetically prepared from phloroglucinol or a derivative of phloroglucinol, being in a monomeric form or/and in a (non-cross-linked or/and cross-linked) polymeric form, has/have a concentration (expressed in terms of weight percent of the total weight of the composition-of-matter) preferably, in a range of between about 0.01 weight percent and about 10 weight percent, more preferably, in a range of between about 0.1 weight percent and about 2 weight percent, and most preferably, in a range of between about 0.4 weight percent and about 1 weight percent. Accordingly, for an exemplary preferred embodiment of the composition-of-matter of the present invention, which includes phloroglucinol in a monomeric form or/and in a (non-cross-linked or/and cross-linked) polymeric form, the phloroglucinol has a concentration preferably, in a range of between about 0.01 weight percent and about 10 weight percent, more preferably, in a range of between about 0.1 weight percent and about 2 weight percent, and most preferably, in a range of between about 0.4 weight percent and about 1 weight percent.

In an exemplary preferred embodiment of the present invention, the composition-of-matter is manufactured in a manner which results in the composition-of-matter including any number of the above described phloroglucinol type compounds optionally being in a monomeric form or/and in a cross-linked polymeric form. For obtaining such an exemplary preferred embodiment, cross-linking of the monomeric form, or/and cross-linking of the polymeric form, of the at least one phloroglucinol type compound is effected by, optionally, using at least one activating agent. More specifically, wherein the cross-linked polymeric form is obtained by, optionally, admixing at least one activating agent with the water miscible polymer and the at least one phloroglucinol type compound, for effecting cross-linking of the monomeric form or/and of the polymeric form.

For implementing such an exemplary preferred embodiment of the present invention, exemplary activating agents are selected from the group consisting of a haloperoxidase (HPO) enzyme, an oxidizer, a halogen salt, and combinations thereof. Exemplary haloperoxidase (HPO) enzymes are bromoperoxidase (BPO), potassium peroxidase (PPO), and combinations thereof. Exemplary oxidizers are peroxides, for example, hydrogen peroxide ($H_2O_2$), strong acids, potassium permanganate, potassium dichromate, and combinations thereof. Exemplary halogen salts are potassium iodide (KI), potassium bromide (KBr), potassium chloride (KCl), sodium iodide (NaI), sodium bromide (NaBr), and sodium chloride (NaCl).

In general, in the composition-of-matter of the present invention, wherein a haloperoxidase (HPO) enzyme, for example, bromoperoxidase (BPO), is used as an activating agent, singly, or in combination with one or more activating agents, for promoting reaction and possible cross-linking, the haloperoxidase (HPO) enzyme has a concentration (expressed in terms of enzyme activity units per ml volume of the composition-of-matter) preferably, in a range of between about 0.1 units/ml and about 5 units/ml, more preferably, in a range of between about 0.5 units/ml and about 2 units/ml, and most preferably, in a range of between about 0.6 units/ml and about 1 unit/ml.

In general, in the composition-of-matter of the present invention, wherein an oxidizer, such as a peroxide, for example, hydrogen peroxide ($H_2O_2$), is used as an activating agent, singly, or in combination with one or more activating agents, for promoting reaction and possible cross-linking, the oxidizer has a concentration (expressed in terms of weight percent of the total weight of the composition-of-matter) preferably, in a range of between about 0.01 weight percent and about 3 weight percent, more preferably, in a range of between about 0.02 weight percent and about 1 weight percent, and most preferably, in a range of between about 0.04 weight percent and about 0.5 weight percent.

In general, in the composition-of-matter of the present invention, wherein a halogen salt, for example, potassium iodide (KI) or potassium bromide (KBr), is used as an activating agent, singly, or in combination with one or more activating agents, for promoting reaction and possible cross-linking, the halogen salt has a concentration (expressed in terms of weight percent of the total weight of the composition-of-matter) preferably, in a range of between about 0.1 weight percent and about 1 weight percent, more preferably, in a range of between about 0.2 weight percent and about 0.7 weight percent, and most preferably, in a range of between about 0.4 weight percent and about 0.6 weight percent.

In general, the water miscible polymer, present in the composition-of-matter of the present invention, in a cross-linked form, is essentially any type or kind of naturally existing polymer or synthetically prepared polymer which is miscible (substantially soluble) in water (in its non cross-linked form).

In an exemplary preferred embodiment of the present invention, the water miscible polymer is a naturally existing, or synthetically prepared, form of a carbohydrate (polysaccharide), such as alginic acid, or/and alginic acid itself. More preferably, the water miscible polymer is a naturally existing, or synthetically prepared, salt form of a carbohydrate (polysaccharide), such as a salt form of alginic acid, being an alginate.

It is noted that, in technical literature of the art, the term 'alginate' is usually used for the salts of alginic acid, but it can also refer to any derivative of alginic acid, as well as alginic acid itself; in some publications the term 'algin' is used instead of alginate. As used herein, the term 'alginate' specifically refers to a salt form of alginic acid.

Alginic acid, and alginates (salt forms of alginic acid) are well known. Alginates are present in cell walls of brown algae, as calcium, magnesium, and sodium, salts of alginic acid. Calcium and magnesium alginate salts do not dissolve in water; sodium alginate salt does.

Figure 3A:
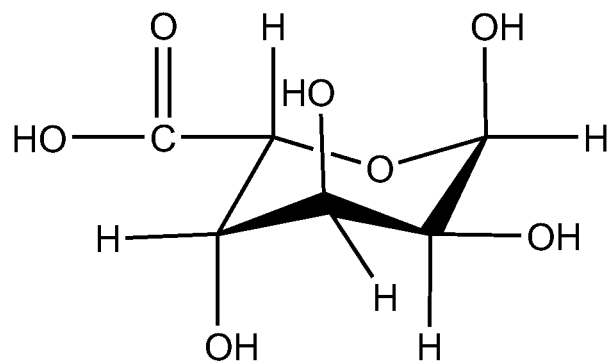
FIGS. 3a and 3b present 2-D schematic illustrations of the chemical structures of the monomer units, alpha-L-glucuronic acid (G) (FIG. 3a) and beta-D-mannuronic acid (M) (FIG. 3b), of alginic acid, being an exemplary water miscible polymer included in a cross-linked form in exemplary preferred embodiments of the composition-of-matter of the present invention.
Figure 3B:
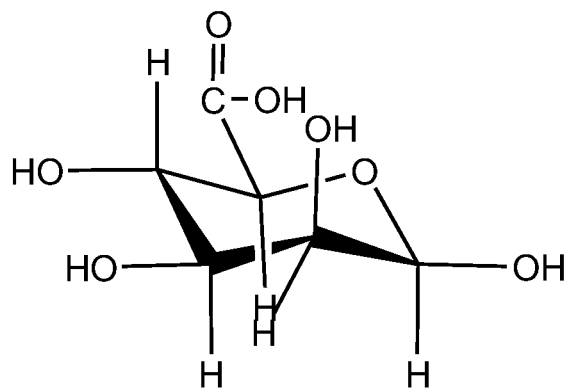

Alginic acid, and alginates, are linear biopolymers composed of two monomeric units: alpha-L-gluronic acid (G) and beta-D-mannuronic acid (M) [24]. FIGS. 3a and 3b present 2-D schematic illustrations of the chemical structures of the monomer units, alpha-L-glucuronic acid (G) (FIG. 3a) and beta-D-mannuronic acid (M) (FIG. 3b), of alginic acid, being an exemplary water miscible polymer included in exemplary preferred embodiments of the composition-of-matter of the present invention.

Alginic acid and alginate polymers are formed by joining these monomer units at the C-1 and C-4 positions. An ether-oxygen bridge joins the carbon at the 1-position in one molecule to the 4-position of another molecule. It is well known that the polymer chain is structured as a block copolymer, made up of three kinds of regions or blocks, with blocks of G and M alternating and interrupted by regions of more random distribution of M and G units. The G blocks contain only units derived from the alpha-L-gluronic acid, the M blocks are based entirely on the beta-D-mannuronic acid, and the MG blocks consist of alternating units from the beta-D-mannuronic acid and the alpha-L-gluronic acid, the proportion of these blocks varying with the algal source. Typical commercially available algae sources include alginic acid and alginate polymers having compositions with either of the beta-D-mannuronic acid (M) units, or the alpha-L-glucuronic acid (G) units, in a range of between about 25 percent and about 75 percent, wherein the corresponding M/G ratio is in a range of between about 0.3 and about 3.

Sizes of the three blocks can vary over a wide range, giving rise to alginates of different properties. Most notably, gels of alginates richer in the G blocks have a higher elastic modulus and also show higher solute diffusivities. Alginates have been extensively investigated for their gelation capabilities in the presence of divalent cations. For example, upon addition of divalent calcium ions ($Ca^{+2}$) to an alginate solution, the chains undergo rearrangement to form so-called egg-box structures, where groups of chain segments align with several intercalating $Ca^{+2}$ ions, leading to a cross-linked polymeric configuration. Calcium alginate gels have been extensively studied and employed in a number of pharmaceutical and biomedical applications, such as drug delivery, wound dressing, and tissue engineering [24].

For implementing the present invention, in general, the alginic acid or alginate polymer is composed of either of the beta-D-mannuronic acid (M) units, or the alpha-L-glucuronic acid (G) units, in a range of between about 25 percent and about 75 percent, wherein the corresponding M/G ratio is in a range of between about 0.3 and about 3. Such alginic acid or alginate compositions are readily, commercially available, including in large quantities which are required for large-scale commercial manufacturing processes. Preferably, the alginic acid or alginate polymer contains the alpha-L-glucuronic acid (G) units in a range of between about 50 percent and about 70 percent, wherein the corresponding M/G ratio is in a range of between about 1 and about 0.43.

For implementing the present invention, exemplary salt forms of alginic acid are alkali metal salts of alginic acid, such as sodium alginate and potassium alginate. Preferably, the alkali metal salt of alginic acid, sodium alginate, is used for implementing the present invention. Preferably, the sodium alginate contains alpha-L-glucuronic acid (G) units in a range of between about 50 percent and about 70 percent, wherein the corresponding M/G ratio is in a range of between about 1 and about 0.43.

In general, the composition-of-matter of the present invention, so formed from manufacturing thereof, as described hereinbelow, includes the cross-linked form of the water miscible polymer. In general, in the composition-of-matter of the present invention, the cross-linked form of the water miscible polymer has a concentration (expressed in terms of weight percent of the total weight of the composition-of-matter) preferably, in a range of between about 0.1 weight percent and about 10 weight percent, more preferably, in a range of between about 0.5 weight percent and about 5 weight percent, and most preferably, in a range of between about 2 weight percent and about 3 weight percent. Accordingly, for an exemplary preferred embodiment of the composition-of-matter of the present invention, wherein the water miscible polymer is the alkali metal salt of alginic acid, sodium alginate, then the sodium alginate has a concentration (expressed in terms of weight percent of the total weight of the composition-of-matter) preferably, in a range of between about 0.1 weight percent and about 10 weight percent, more preferably, in a range of between about 0.5 weight percent and about 5 weight percent, and most preferably, in a range of between about 2 weight percent and about 3 weight percent.

For an embodiment of the composition-of-matter of the present invention, wherein the water miscible polymer is an alginate, or alginic acid, preferably, the alginate, or the alginic acid, is cross-linked via interaction with divalent ions. Exemplary divalent ions which are suitable for implementing the present invention are divalent ions of alkaline earth elements. For example, divalent calcium ions ($Ca^{+2}$), divalent magnesium ions ($Mg^{+2}$), divalent strontium ions ($Sr^{+2}$), and divalent barium ions ($Ba^{+2}$), of the corresponding alkaline earth elements, calcium (Ca), magnesium (Mg), strontium (Sr), and barium (Ba), respectively. Exemplary sources of these divalent ions are halogen salts of the alkaline earth elements, such as calcium chloride ($CaCl_2$), magnesium chloride ($MgCl_2$), strontium chloride ($SrCl_2$), and barium chloride ($BaCl_2$). Another exemplary specific source of divalent calcium ions ($Ca^{+2}$) is provided by a combination of calcium carbonate ($CaCO_3$) and glucono-δ-lactone (GDL) [25].

In general, the alginate or alginic acid salt can be cross-linked with other divalent ions. Preferably, the alginate, or alginic acid, is cross-linked with divalent calcium ions ($Ca^{+2}$). In an exemplary preferred embodiment of the composition-of-matter of the present invention, wherein divalent ions, for example, divalent calcium ions ($Ca^{+2}$), are used for promoting cross-linking of the water miscible polymer, wherein the water miscible polymer is, for example, sodium alginate, the divalent calcium ions ($Ca^{+2}$) are preferably supplied by calcium chloride ($CaCl_2$), having a concentration (expressed in terms of weight percent of the total weight of the composition-of-matter) preferably, in a range of between about 0.01 weight percent and about 2 weight percent, more preferably, in a range of between about 0.05 weight percent and about 1 weight percent, and most preferably, in a range of between about 0.1 weight percent and about 0.5 weight percent.

As described hereinbelow, in general, any of the above described preferred embodiments or formulations of the composition-of-matter of the present invention is usable as an adhesive, of a variety of different types of surfaces, under dry conditions or under wet conditions, whereby the adhesive composition-of-matter exhibits adhesive properties, characteristics, and behavior. As illustratively described in detail in the Examples section, hereinbelow, shear or tensile type adhesive strength of selected formulations of the adhesive composition of the present invention, under dry or wet conditions, was measured using the Shear Lap Test (Examples 1-10) or the Tensile Test (Examples 11-15), respectively, being two of the most commonly known and used techniques for evaluating adhesive bond strength, with a Lloyd tensile instrument equipped with a 50N load cell.

In general, any of the above described preferred embodiments or formulations of the composition-of-matter of the present invention, preferably, has an adhesive strength (for example, as measured using the Shear Lap Test or the Tensile Test with a Lloyd tensile instrument), preferably, of at least about 5 kPa, more preferably, of at least about 35 kPa, and most preferably, of at least 100 kPa.

For any of the above described preferred embodiments or formulations of the composition-of-matter of the present invention generally usable as an adhesive, the adhesive may be functional and usable as a sealant or sealing agent, for sealing or closing an opening in a (dry or wet) surface, for example, for preventing flow of a (liquid or/and gaseous) fluid through the sealed or closed portion of the surface. Accordingly, the sealing or closing may take place under dry or wet conditions. The surface having the opening which is sealed or closed may be a body part or a component thereof (e.g., a tissue), of a human or animal subject. Such a sealant or sealing agent can be used in a wide variety of applications, for example, for sealing or closing an opening in a (dry or wet) body part, or in a (dry or wet) surface of a medical device, of an aquarium, or of a wide variety of other objects or entities.

Another main aspect of the present invention is provision of a method of manufacturing the composition-of-matter, as described hereinabove, of the present invention, the method including the procedures of: providing a water-miscible polymer; providing a cross-linking agent; providing the at least one phloroglucinol type compound; and mixing the water miscible polymer, the cross-linking agent and the at least one phloroglucinol type compound, thereby obtaining the composition-of-matter.

In general, the composition-of-matter, as described hereinabove, of the present invention, is manufactured by using standard procedures and techniques well known in the art of mixing chemicals and chemical reagents for the purpose of forming a chemical product.

As described hereinabove, preferred embodiments or formulations of the composition-of-matter of the present invention are composed of any of a variety of different combinations of a water miscible polymer and at least one phloroglucinol type compound selected from the group consisting of: phloroglucinol, a derivative of phloroglucinol, and a polymer synthetically prepared from phloroglucinol or a derivative of phloroglucinol.

Accordingly, the corresponding different preferred embodiments or formulations of the composition-of-matter are manufactured by the following corresponding different preferred embodiments of the method of the present invention:

mixing the water miscible polymer with the phloroglucinol.

mixing the water miscible polymer with the at least one derivative of phloroglucinol.

mixing the water miscible polymer with the at least one polymer synthetically prepared from phloroglucinol or a derivative of phloroglucinol or a polymer (e.g., oligomer) thereof.

mixing the water miscible polymer with the phloroglucinol, and the at least one derivative of phloroglucinol.

mixing the water miscible polymer with the phloroglucinol, and the at least one polymer synthetically prepared from phloroglucinol or a derivative of phloroglucinol or a polymer (e.g., oligomer) thereof.

mixing the water miscible polymer with the phloroglucinol, the at least one derivative of phloroglucinol, and the at least one polymer synthetically prepared from phloroglucinol or a derivative of phloroglucinol or a polymer (e.g., oligomer) thereof.

For manufacturing any of the above stated preferred embodiments or formulations of the composition-of-matter of the present invention, concentration ranges of each of the components, that is, the water miscible polymer, the phloroglucinol, the derivative of phloroglucinol, and the polymer synthetically prepared from phloroglucinol or a derivative of phloroglucinol, correspond to those previously provided hereinabove, with regard to describing the composition-of-matter of the present invention.

Any of the above stated preferred embodiments or formulations of the composition-of-matter of the present invention, can be manufactured in a manner wherein the composition-of-matter includes any number of the above described phloroglucinol type compounds in a monomeric form or/and in a (non-cross-linked or/and cross-linked) polymeric form. More specifically, the composition-of-matter of the present invention, so formed from manufacturing thereof, as described herein, includes at least one phloroglucinol type compound selected from the group consisting of: phloroglucinol, a derivative of phloroglucinol, and a polymer synthetically prepared from phloroglucinol or a derivative of phloroglucinol, in a monomeric form or/and in a (non-cross-linked or/and cross-linked) polymeric form.

Accordingly, the method of manufacturing the composition-of-matter of the present invention, optionally, also includes mixing the components with at least one activating agent. As previously stated, hereinabove, such activating agents, optionally, can be used for promoting radical reactions that possibly lead to cross-linking, or/and oxidation, or/and some other modification, of any of the phloroglucinol type compounds. The cross-linking of a monomeric form or/and the cross-linking of a polymeric form, of any of the phloroglucinol type compounds is effected by at least one activating agent. Accordingly, in such an exemplary preferred embodiment, optionally, at least one activating agent is used in the manufacturing method for promoting reaction and possible cross-linking, or/and oxidation, or/and some other modification, of any of the phloroglucinol type compounds, for forming the composition-of-matter of the present invention. More specifically, wherein the cross-linked polymeric form is obtained by, optionally, admixing at least one activating agent with the water miscible polymer and the at least one phloroglucinol type compound, for effecting cross-linking of a monomeric form or/and cross-linking of a polymeric form.

For implementing such an exemplary preferred embodiment of the manufacturing method of the present invention, exemplary activating agents are selected from the group consisting of a haloperoxidase (HPO) enzyme, an oxidizer, a halogen salt, and combinations thereof. Exemplary haloperoxidase (HPO) enzymes are bromoperoxidase (BPO), potassium peroxidase (PPO), and combinations thereof. Exemplary oxidizers are peroxides, for example, hydrogen peroxide ($H_2O_2$), strong acids, potassium permanganate, potassium dichromate, and combinations thereof. Exemplary halogen salts are potassium iodide (KI), potassium bromide (KBr), potassium chloride, sodium iodide (NaI), sodium bromide (NaBr), and sodium chloride (NaCl).

In such an exemplary preferred embodiment, the method of manufacturing the composition-of-matter of the present invention, includes mixing the components (the water miscible polymer and the at least one phloroglucinol type compound) with a haloperoxidase (HPO) enzyme, for example, bromoperoxidase (BPO), and an oxidizer, for example, hydrogen peroxide ($H_2O_2$), and a halogen salt, for example, potassium iodide (KI) or potassium bromide (KBr), for forming the composition-of-matter including any number of the above described phloroglucinol type compounds being in a cross-linked polymeric form.

In such an exemplary preferred embodiment of the method of manufacturing the composition-of-matter of the present invention, concentration ranges of each of the at least one activating agent, that is, the haloperoxidase (HPO) enzyme, the oxidizer, and the halogen salt, correspond to those previously provided hereinabove, with regard to describing the composition-of-matter of the present invention.

For manufacturing any of the above stated preferred embodiments or formulations of the composition-of-matter of the present invention, there is using any type or kind of the water miscible polymer previously described hereinabove, with regard to describing the composition-of-matter of the present invention.

In particular, preferably, the water miscible polymer is a naturally existing, or synthetically prepared, form of a carbohydrate (polysaccharide), such as alginic acid, or/and alginic acid itself. More preferably, the water miscible polymer is a naturally existing, or synthetically prepared, salt form of a carbohydrate (polysaccharide), such as a salt form of alginic acid, being an alginate. The alginic acid or alginate polymer used in the manufacturing method of the present invention has the various properties, characteristics, and behavior, as well as concentration ranges, as previously described and provided hereinabove, with regard to describing the composition-of-matter of the present invention. In particular, the alginic acid or alginate polymer has a composition with either of the beta-D-mannuronic acid (M), or the alpha-L-glucuronic acid (G), in a range of between about 25 percent and about 75 percent, wherein the corresponding M/G ratio is in a range of between about 0.3 and about 3. Such alginic acid or alginate compositions are readily, commercially available, including in large quantities which are required for large-scale commercial manufacturing processes. Preferably, the alginic acid or the alginate polymer has a composition with the alpha-L-glucuronic acid (G) in a range of between about 50 percent and about 70 percent, wherein the corresponding M/G ratio is in a range of between about 1 and about 0.43.

For implementing the manufacturing method of the present invention, exemplary salt forms of alginic acid are alkali metal salts of alginic acid, such as sodium alginate and potassium alginate. Preferably, the alkali metal salt of alginic acid, sodium alginate, is used for implementing the manufacturing method of the present invention. Preferably, the sodium alginate has a composition with the alpha-L-glucuronic acid (G) in a range of between about 50 percent and about 70 percent, wherein the corresponding M/G ratio is in a range of between about 1 and about 0.43.

In general, the method of manufacturing the composition-of-matter of the present invention, is performed in a manner wherein the resulting water miscible polymer in the composition-of-matter is in a non-cross-linked form or/and in a cross-linked form. For manufacturing the composition-of-matter of the present invention, wherein the resulting water miscible polymer is an alginate, or alginic acid, preferably, the resulting alginate (for example, sodium alginate), or the alginic acid, is cross-linked with divalent ions. Accordingly, in such an embodiment, the manufacturing method includes mixing the components with at least one type of divalent ions.

Exemplary divalent ions which are suitable for implementing the manufacturing method of the present invention are divalent ions of alkaline earth elements. For example, divalent calcium ions ($Ca^{+2}$), divalent magnesium ions ($Mg^{+}_2$), divalent strontium ions ($Sr^{+2}$), and divalent barium ions ($Ba^{+2}$), of the corresponding alkaline earth elements, calcium (Ca), magnesium (Mg), strontium (Sr), and barium (Ba), respectively. Exemplary sources of these divalent ions are halogen salts of the alkaline earth elements, such as calcium chloride ($CaCl_2$), magnesium chloride ($MgCl_2$), strontium chloride ($SrCl_2$), and barium chloride ($BaCl_2$).

In general, other divalent ions can be used in the manufacturing method for cross-linking the alginate or alginic acid salt. Preferably, the alginate, or alginic acid, is cross-linked with divalent calcium ions ($Ca^{+2}$). In an exemplary preferred embodiment of the manufacturing method of the present invention, wherein divalent ions, for example, divalent calcium ions ($Ca^{+2}$), are used for promoting cross-linking of the water miscible polymer, wherein the water miscible polymer is, for example, sodium alginate, the divalent calcium ions ($Ca^{+2}$) are preferably supplied by calcium chloride ($CaCl_2$), having a concentration in any of the ranges previously provided hereinabove, with regard to describing the composition-of-matter of the present invention.

In an exemplary preferred embodiment of the manufacturing method, the composition-of-matter of the present invention can be prepared as a solution, for example, by dissolving, via mixing, in water a mixture of a quantity of each of the following components, in the indicated 'exemplary' order:

at least one phloroglucinol type compound selected from the group consisting of: phloroglucinol, a derivative of phloroglucinol, and a polymer synthetically prepared from phloroglucinol or a derivative of phloroglucinol, for example, phloroglucinol (1,3,5-trihydroxybenzene) in a monomeric form.

at least one activating agent, for example, a haloperoxidase (HPO) enzyme, in particular, bromoperoxidase (BPO); an oxidizer, for example, hydrogen peroxide ($H_2O_2$); and a halogen salt, for example, potassium iodide (KI) or potassium bromide (KBr).

a water miscible polymer, for example, a salt of alginic acid (an alginate), in particular, sodium alginate.

a cross-linking agent (for the water miscible polymer), for example, divalent ions, in particular, divalent calcium ions ($Ca^{+2}$) supplied, for example, by calcium chloride ($CaCl_2$), or by a combination of calcium carbonate ($CaCO_3$) and glucono-δ-lactone (GDL).

For manufacturing any of the above stated embodiments and formulations of the composition-of-matter of the present invention, the individual components are either used 'as is' in a solid particulate form, from which a mass aliquot is weighed out, or, is used in the form of a small volume laboratory scale stock solution or a large volume commercial scale stock solution, from which a volumetric aliquot is taken.

In an exemplary preferred embodiment of the manufacturing method, phloroglucinol, in a monomeric form, and the water miscible polymer, being sodium alginate, are each used as is in solid particulate forms, whereas, the haloperoxidase enzyme type of activating agent, being bromoperoxidase (BPO), the oxidizer type of activating agent, being hydrogen peroxide ($H_2O_2$), and the halogen salt type of activating agent, being potassium iodide (KI) or potassium bromide (KBr), and the source of the divalent ions type of alginate cross-linking agent, being calcium chloride ($CaCl_2$), or a combination of calcium carbonate ($CaCO_3$) and glucono-δ-lactone (GDL), are used in the form of a small volume laboratory scale stock solution or a large volume commercial scale stock solution, from which a volumetric aliquot is taken.

As previously stated hereinabove, it is to be understood that the method of manufacturing the composition-of-matter of the present invention is not limited in its application to the above described details of the components of the disclosed composition-of-matter, or to the above described details of the order or sequence, and number, of procedures, steps, and sub-steps, or of the materials used.

As previously stated hereinabove, the present inventors sought to overcome significant limitations currently associated with large-scale commercial availability of naturally existing adhesive raw materials, such as polyphenols, and corresponding limitations associated with manufacturing usable forms of adhesives therefrom. The manufacturing method of the present invention, for manufacturing the composition-of-matter of the present invention, is commercially feasible and applicable, and doesn't require processing an enormous quantity of a marine or aquatic organism, followed by having to perform a relatively long sequence of various chemical and physical separation and purification processes and procedures, for producing a usable final form of the inventive adhesive.

Another main aspect of the present invention is provision of a use of the composition-of-matter, as described hereinabove, of the present invention, as an adhesive.

In general, any of the above described preferred embodiments or formulations of the composition-of-matter of the present invention is usable as an adhesive. As previously stated, hereinabove, it is to be fully understood that as used herein, the term 'adhesive' is synonymous with the term 'glue', whereby each refers to a material or substance which exhibits adhesive properties, characteristics, and behavior. Accordingly, herein, an adhesive synonymously and equivalently refers to a glue, and use of the term adhesive is meant to generally encompass either such term. Accordingly, in general, any of the above described preferred embodiments or formulations of the composition-of-matter of the present invention is usable as a glue.

Any of the above described preferred embodiments or formulations of the composition-of-matter of the present invention is generally usable as an adhesive, of a variety of different types of surfaces, under dry conditions or under wet conditions. In general, any of the above described preferred embodiments or formulations of the composition-of-matter of the present invention is generally usable as an adhesive, of a variety of different types of surfaces, under dry conditions or under wet conditions. The adhesive, preferably, has an adhesive strength (for example, as measured using the Shear Lap Test or Tensile Test with a Lloyd tensile instrument) preferably, of at least about 5 kPa, more preferably, of at least about 35 kPa, and most preferably, of at least 100 kPa.

In particular, the composition-of-matter of the present invention is generally usable as an adhesive under dry conditions, for example, for adhering a first surface to a second surface, wherein each of the first surface and the second surface is dry. Herein, the term 'dry' is used in the context wherein a designated area of the first surface upon which a quantity of the adhesive is applied, 'and' at least a portion of the second surface which contacts the designated area, for adhering the first surface to the second surface, are each essentially absent of a liquid or vapor phase fluid.

Alternatively, and advantageously, the composition-of-matter of the present invention is generally usable as an adhesive under wet conditions, for example, for adhering a first surface to a second surface, wherein the first surface is wet or/and the second surface is wet. Herein, the term 'wet' is used in the context wherein a designated area of the first surface upon which a quantity of the adhesive is applied, 'or/and' at least a portion of the second surface which contacts the designated area, for adhering the first surface to the second surface, is/are at least partly wetted by a liquid or vapor phase fluid.

For using the composition-of-matter of the present invention as an adhesive, under dry or wet conditions, for adhering a first surface to a second surface, a sufficient period of time is required for enabling the designated area of the first surface to adhere to that portion of the second surface which contacts the designated area. Such a sufficient period of time is preferably on the order of at least about one minute, more preferably, of at least about five minutes, and most preferably, of at least about ten minutes.

It is to be understood that, in a non-limiting manner, each of the first surface and the second surface can be made or composed of essentially any type or kind of material or substance, including, for example, essentially any type or kind of inorganic material or substance, or essentially any type or kind of organic material or substance, for example, a body part or a component thereof, such as tissue, of a (human or animal) subject.

Any of the above described preferred embodiments or formulations of the composition-of-matter of the present invention is generally usable as an adhesive, of a variety of different types of surfaces, under dry conditions or under wet conditions, in a wide variety of different fields, for example, in the health care fields of medicine, dentistry, and veterinary science, as well as in other fields, such as general industry for commercial use, for laboratory use, or for home use.

Any of the above described preferred embodiments or formulations of the composition-of-matter of the present invention is particularly usable as an adhesive, of a variety of different types of surfaces, under dry conditions or under wet conditions, in the health care fields of medicine, dentistry, and veterinary science, especially for use by health care providers, such as medical, dental, and veterinary, surgeons, in procedures for reattaching or repairing body parts or components thereof, such as tissue, of (human or animal) subjects, especially under wet conditions, for example, involving adhesion of wet surfaces.

For any of the above described preferred embodiments or formulations of the composition-of-matter of the present invention generally usable as an adhesive, the adhesive may be functional and usable as a sealant or sealing agent, for sealing or closing an opening in a (dry or wet) surface, for example, for preventing flow of a (liquid or/and gaseous) fluid through the sealed or closed portion of the surface. Accordingly, the sealing or closing may take place under dry or wet conditions. The surface having the opening which is sealed or closed may be a body part or a component thereof (e.g., a tissue), of a human or animal subject.

It is to be understood that, in a non-limiting manner, the surface having the opening can be made or composed of essentially any type or kind of material or substance, including, for example, essentially any type or kind of inorganic material or substance, or essentially any type or kind of organic material or substance, for example, a body part or a component thereof, such as tissue, of a (human or animal) subject. Such a sealant or sealing agent can be used in a wide variety of applications, for example, for sealing or closing an opening in a (dry or wet) body part, or in a (dry or wet) surface of a medical device, of an aquarium, or of a wide variety of other objects or entities.

Any of the above described preferred embodiments or formulations of the composition-of-matter of the present invention is generally usable as an adhesive, which may be functional and usable as a sealant or sealing agent, of a variety of different types of surfaces, under dry conditions or under wet conditions, in a wide variety of different fields, for example, in the health care fields of medicine, dentistry, and veterinary science, as well as in other fields, such as general industry for commercial use, for laboratory use, or for home use.

Any of the above described preferred embodiments or formulations of the composition-of-matter of the present invention is generally usable as an adhesive, which may be functional and usable as a sealant or sealing agent, of a variety of different types of surfaces, under dry conditions or under wet conditions, in the health care fields of medicine, dentistry, and veterinary science, especially for use by health care providers, such as medical, dental, and veterinary, surgeons, in procedures for sealing or closing an opening in a body part or component thereof, such as tissue, of (human or animal) subjects, especially under wet conditions, for example, involving sealing or closing an opening in a wet surface.

Another main aspect of the present invention is provision of a method of adhering a first surface to a second surface, the method including the procedure of applying an effective amount of the composition-of-matter, as described hereinabove, of the present invention upon a designated area of the first surface, contacting the designated area with at least a portion of the second surface, and providing a sufficient period of time for the first surface to adhere to the second surface, thereby adhering the first surface to the second surface.

Any of the above described preferred embodiments or formulations of the composition-of-matter of the present invention is generally usable as an adhesive, under dry conditions or under wet conditions, for implementing the method of adhering a first surface to a second surface.

Any of the above described preferred embodiments or formulations of the composition-of-matter of the present invention is generally usable as an adhesive, under dry conditions or under wet conditions, for implementing the method of adhering a first surface to a second surface. The composition-of-matter, preferably, has an adhesive strength (for example, as measured using the Shear Lap Test or Tensile Test with a Lloyd tensile instrument), preferably, of at least about 5 kPa, more preferably, of at least about 35 kPa, and most preferably, of at least 100 kPa.

In particular, in the procedure, under dry conditions, for example, wherein adhering the first surface to the second surface, each of the first and second surfaces is dry. As previously stated hereinabove, the term 'dry' is used in the context wherein a designated area of the first surface upon which a quantity of the composition-of-matter of the present invention is applied, 'and' at least a portion of the second surface which contacts the designated area, for adhering the first surface to the second surface, are each essentially absent of a liquid or vapor phase fluid.

Alternatively, in particular, in the procedure, under wet conditions, for example, wherein adhering the first surface to the second surface, wherein the first surface is wet or/and the second surface is wet. As previously stated hereinabove, the term 'wet' is used in the context wherein a designated area of the first surface upon which a quantity of the composition-of-matter of the present invention is applied, 'or/and' at least a portion of the second surface which contacts the designated area, for adhering the first surface to the second surface, is/are at least partly wetted by a liquid or vapor phase fluid.

For implementing the method of adhering the first surface to the second surface, a sufficient period of time is required for enabling the designated area of the first surface to adhere to that portion of the second surface which contacts the designated area. Such a sufficient period of time is preferably on the order of at least about one minute, more preferably, of at least about five minutes, and most preferably, of at least about ten minutes.

It is to be understood that, in a non-limiting manner, each of the first surface and the second surface can be made or composed of essentially any type or kind of material or substance, including, for example, essentially any type or kind of inorganic material or substance, or essentially any type or kind of organic material or substance, for example, a body part or a component thereof, such as tissue, of a (human or animal) subject.

The method of adhering a first surface to a second surface, performed under dry conditions or under wet conditions, is generally applicable in a wide variety of different fields, for example, in the health care fields of medicine, dentistry, and veterinary science, as well as in other fields, such as general industry for commercial use, for laboratory use, or for home use.

The method of adhering a first surface to a second surface, performed under dry conditions or under wet conditions, is generally applicable in the health care fields of medicine, dentistry, and veterinary science, especially for use by health care providers, such as medical, dental, and veterinary, surgeons, in procedures for reattaching or repairing body parts or components thereof, such as tissue, of (human or animal) subjects, especially under wet conditions, for example, involving adhesion of wet surfaces.

Another main aspect of the present invention is provision of an article-of-manufacture which includes (a) a packaging material, and (b) the composition-of-matter, as described hereinabove, of the present invention, being contained within the packaging material, wherein the composition-of-matter is identified for use as an adhesive.

In general, any of the above described preferred embodiments or formulations of the composition-of-matter of the present invention is suitable as being contained within the packaging material, wherein the composition-of-matter is identified for use as an adhesive, in particular, as described hereinabove. For any of the above described preferred embodiments or formulations of the composition-of-matter of the present invention generally usable as an adhesive, the adhesive may be functional and usable as a sealant or sealing agent, for sealing or closing an opening in a (dry or wet) surface, in particular, as described hereinabove.

Above illustratively described novel and inventive aspects and characteristics, and advantages thereof, of the present invention further become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Reference is now made to the following examples, which together with the above descriptions, illustrate the invention in a non-limiting fashion.

Materials and Experimental Methods

Materials:

Phloroglucinol (1,3,5-trihydroxybenzene) monomer-synthetic form, bromoperoxidase (BPO) (0.7 units/ml, from corallina officinalis), and hydrogen peroxide ($H_2O_2$), 30 percent, were obtained from Sigma-Aldrich. Potassium iodide (KI) and potassium bromide (KBr) were obtained from Spectrum Chemical. Calcium chloride ($CaCl_2$), 1M standard solution, was obtained from Fluka. Calcium carbonate ($CaCO_3$), powder form, was obtained from Fluka. Glucono-b-lactone (GDL), powder form, was obtained from Fluka.

Two types of sodium alginate were used: (1) Protanal LF 200 S, with G content of about 70 percent, and (2) Protanal HF 120 RBS, with G content of about 50 percent. Milli-Q purified deionized water was used throughout.

Preparation of Formulations of the Adhesive Composition:

Samples of various different specific formulations of the adhesive composition of the present invention were prepared, and then subjected to NMR, and, shear or tensile type adhesive strength measurements. For comparative purposes, reference samples were also prepared and subjected to the NMR, or/and, shear or tensile type adhesive strength measurements.

Samples of formulations of the adhesive composition of the present invention were prepared as solutions, by dissolving, via mixing, in water, a mixture of a quantity of each of the following components, according to the indicated 'exemplary' (i.e., not required) order:

(a) at least one phloroglucinol type compound selected from the group consisting of: phloroglucinol, a derivative of phloroglucinol, and a polymer synthetically prepared from phloroglucinol or a derivative of phloroglucinol: phloroglucinol (1,3,5-ffihydroxybenzene) monomer (synthetic form) was used.

(b) with or without at least one (optional) activating agent:
(i) a haloperoxidase (HPO) enzyme: bromoperoxidase (BPO) was used.
(ii) an oxidizer: hydrogen peroxide ($H_2O_2$) was used.
(iii) a halogen salt: potassium iodide (KI) or potassium bromide (KBr) was used.

(c) a water miscible polymer: a salt of alginic acid (an alginate): sodium alginate was used.

(d) a cross-linking agent (for the water miscible polymer): divalent ions, divalent calcium ($Ca^{+2}$) ions, from a calcium salt: calcium chloride ($CaCl_2$), or a combination of calcium carbonate ($CaCO_3$) and glucono-δ-lactone (GDL), was used.

In Examples 1-10, the formulation of each adhesive composition was prepared using (optional) activating agents, indicated just above by addition of component (b)—at least one (optional) activating agent: (i), (ii), or/and (iii). In Examples 11-15, the formulation of each adhesive composition was prepared without using (optional) activating agents.

The individual components were either used 'as is' in a solid particulate form, from which a mass aliquot was weighed out, or, were used in the form of a laboratory stock solution from which a volumetric aliquot was taken, for preparing samples of the solution formulations of the adhesive composition. The phloroglucinol monomer (synthetic form) and the sodium alginate were used 'as is' in solid particulate forms, whereas bromoperoxidase (BPO), hydrogen peroxide ($H_2O_2$), potassium iodide (KI) or potassium bromide (KBr), and calcium chloride ($CaCl_2$), were used in the form of laboratory stock solutions, for preparing samples of the solution formulations of the adhesive composition.

The following laboratory stock solutions were prepared for each of bromoperoxidase (BPO), hydrogen peroxide ($H_2O_2$), potassium iodide (KI), potassium bromide (KBr), calcium chloride ($CaCl_2$), calcium carbonate ($CaCO_3$) (suspension), and glucono-δ-lactone (GDL):

bromoperoxidase (BPO) solution (1 ml of 0.0089 mg/ml (0.7 units/ml) in 1 ml water).
hydrogen peroxide ($H_2O_2$) solution (0.5 ml of 30 percent solution in 8 ml water).
potassium iodide (KI) solution (4.4 mg in 50 ml water)
potassium bromide (KBr) solution (4.4 mg in 50 ml water).
calcium chloride ($CaCl_2$) solution (10 ml of 1M solution in 90 ml water).
calcium carbonate ($CaCO_3$) suspension, 15 mM.
glucono-δ-lactone (GDL) solution, 30 mM.

Weighed out mass aliquots, or volumetric aliquots of the laboratory stock solutions, of the individual components, were added in the exemplary indicated order to a 0.5 ml plastic microcentrifuge tube, with mixing after each component addition. For comparative purposes, for preparing some samples of the solution formulations of the adhesive composition, which were subjected to adhesive strength measurements, a selected individual component was omitted.

Nuclear Magnetic Resonance ($^1H$ NMR):
Nucleic magnetic resonance ($^1H$ NMR) measurements were recorded at 500 MHz, using a Bruker NMR instrument. All NMR measurements were made at about 25° C. Optimal quality of the $^1H$ spectra was obtained by using selective gated saturation which suppressed the solvent signal ($H_2O$).

Shear Type Adhesive Strength (Under Dry or Wet Conditions):

Shear type adhesive strength of selected formulations of the adhesive composition of the present invention, under dry or wet conditions, was measured using the Shear Lap Test, being one of the most commonly known and used techniques for evaluating shear type adhesive bond strength. A Lloyd tensile instrument equipped with a 50N load cell was used for performing the Shear Lap Test. FIGS. 4a and 4b are pictorial diagrams illustrating formation (FIG. 4a) of a typical 'sandwich' type of specimen as a shear type 'adhesive joint' (FIG. 4b) in a specimen holder, for performing the Shear Lap Test, for measuring shear type adhesive strength of selected formulations of the adhesive composition-of-matter of the present invention, under dry or wet conditions.

Shear type adhesive strength of selected formulations of the adhesive composition was measured for specimens in the form of a 'sandwich' of either two (dry) Mylar™ strips (Pronat, Israel), or of two (dry or wet) collagen films (Devro Teepak, 60 percent collagen), with a quantity of a sample of a formulation of the adhesive composition of the present invention having been applied onto a small surface area near the edge of one of the Mylar strips, or of one of the collagen films, prior to forming the sandwich.

Each Mylar sandwich specimen was prepared from two Mylar™ rectangular strips, each having dimensions of 50 mm length, 15 mm width, and 0.1 mm thickness. For preparing each collagen sandwich specimen, each collagen film was first wetted by immersion in water, then, the back side of each collagen film was pasted, using a synthetic glue, onto a separate Mylar strip for support. A quantity (1 μl) of a sample of a formulation of the adhesive composition of the present invention was applied onto a 5 mm×5 mm surface area near the edge of one of the Mylar strips or collagen films. Immediately following application of the adhesive composition onto the indicated surface area of the first Mylar strip or collagen film, then, the second Mylar strip or collagen film was placed on top of the first Mylar strip or collagen film, respectively. Each sandwich specimen was then pressed under a load of 0.5 kg for 12 minutes, and immediately thereafter, under a load of 1 kg for 3 minutes. Two hours following preparation of a given Mylar or collagen sandwich specimen, the Lap Shear Test was performed with the Lloyd tensile instrument. The force (pressure) necessary to separate the two Mylar strips or the two collagen films (supported on Mylar strips), of a given Mylar or collagen sandwich specimen, respectively, was determined at a crosshead speed of 1 mm/minute. The separation force (pressure), measured in units of kPa, corresponds to the shear type adhesive strength of a given formulation of the adhesive composition of the present invention.

Tensile Type Adhesive Strength (Under Dry Conditions):

Tensile type adhesive strength of selected formulations of the adhesive composition of the present invention, under dry conditions, was measured using a Tensile Test, for evaluating tensile type adhesive bond strength. A Lloyd tensile instrument equipped with a 50N load cell was used for performing the Tensile Test. FIGS. 4c and 4d are pictorial diagrams illustrating formation (FIG. 4c) of a typical 'sandwich' type of specimen as a tensile type 'adhesive joint' (FIG. 4d) in a specimen holder, for performing the Tensile Test, for measuring tensile type adhesive strength of selected formulations of the adhesive composition-of-matter of the present invention, under dry conditions.

Tensile type adhesive strength of selected formulations of the adhesive composition was measured for specimens in the form of a 'sandwich' of two (dry) Mylar strips, or, of two (dry) collagen films (Devro Teepak, 60 percent collagen), or, of two (dry) (microscope) glass slides, or, of two (dry) polystyrene Petri dishes, or, of two pieces of animal tissue (chicken breast), with a quantity of a sample of a formulation of the adhesive composition of the present invention having been applied onto a small surface area near the center of one of the (dry) Mylar strips, or, of one of the (dry) collagen films, or, of one of the (dry) (microscope) glass slides, or, of one of the (dry) polystyrene Petri dishes, or, of one of the pieces of animal tissue, prior to forming the sandwich.

In the examples (Examples 11-15) of measuring the tensile type adhesive strength, each of the Mylar, collagen, glass, polystyrene, or animal tissue, sandwich specimens was prepared in a manner similar to that described hereinabove, for preparing the Mylar or collagen sandwich specimens used for measuring the Shear type adhesive strength.

A quantity (1 μl) of a sample of a formulation of the adhesive composition of the present invention was applied onto a 2.5 cm×2.5 cm surface area near the center of one of the Mylar strips, or, of one of the collagen films, or, of one of the glass slides, or, of one of the polystyrene Petri dishes, or, of one of the pieces of animal tissue. Immediately following application of the adhesive composition onto the indicated surface area of the first of each of the Mylar strips, or, of the collagen films, or, of the glass slides, or, of the polystyrene Petri dishes, or, of the pieces of animal tissue, then, the second Mylar strip, or, collagen film, or, glass slide, or, polystyrene Petri dish, or, piece of animal tissue, was placed on top of the first Mylar strip, or, of collagen film, or, glass slide, or, polystyrene Petri dish, or, piece of animal tissue, respectively.

Each sandwich specimen was then pressed under a load of 0.5 kg for 12 minutes, and immediately thereafter, under a load of 1 kg for 3 minutes. Two hours following preparation of a given sandwich specimen, the Tensile Test was performed with the Lloyd tensile instrument. The force (pressure) necessary to separate the two Mylar strips, or, the two collagen films, or, the two glass slides, or, the two polystyrene Petri dishes, or, the two pieces of animal tissue, of each respective sandwich specimen, was then determined. The separation force (pressure), measured in units of kPa, corresponds to the tensile type adhesive strength of a given formulation of the adhesive composition of the present invention.

Experimental Results

Nuclear Magnetic Resonance ($^1$H NMR):

NMR measurements were made for attempting to obtain information regarding the molecular structures of formulations of the adhesive composition of the present invention, and for attempting to identify the possible influence, if present, and extent thereof, that the individual components [phloroglucinol monomer; activating agents: haloperoxidase (for example, bromoperoxidase), oxidizer (for example, $H_2O_2$), halogen salt (for example, KI or KBr); water miscible polymer: alginate (for example, sodium alginate); and cross-linking agent: divalent ions (for example, divalent calcium ($Ca^{+2}$), from a calcium salt, for example, $CaCl_2$)], may have on the properties, characteristics, and behavior, of the adhesive formulations of the present invention. In accordance with the extent or degree of varying the concentration of a given component of an adhesive formulation, such variation of the component is expected to influence and possibly change, to a varying extent or degree, the molecular structure of the adhesive, and therefore, the physicochemical environment of the protons of the adhesive formulation, which could be detectable by NMR.

Figure 5:
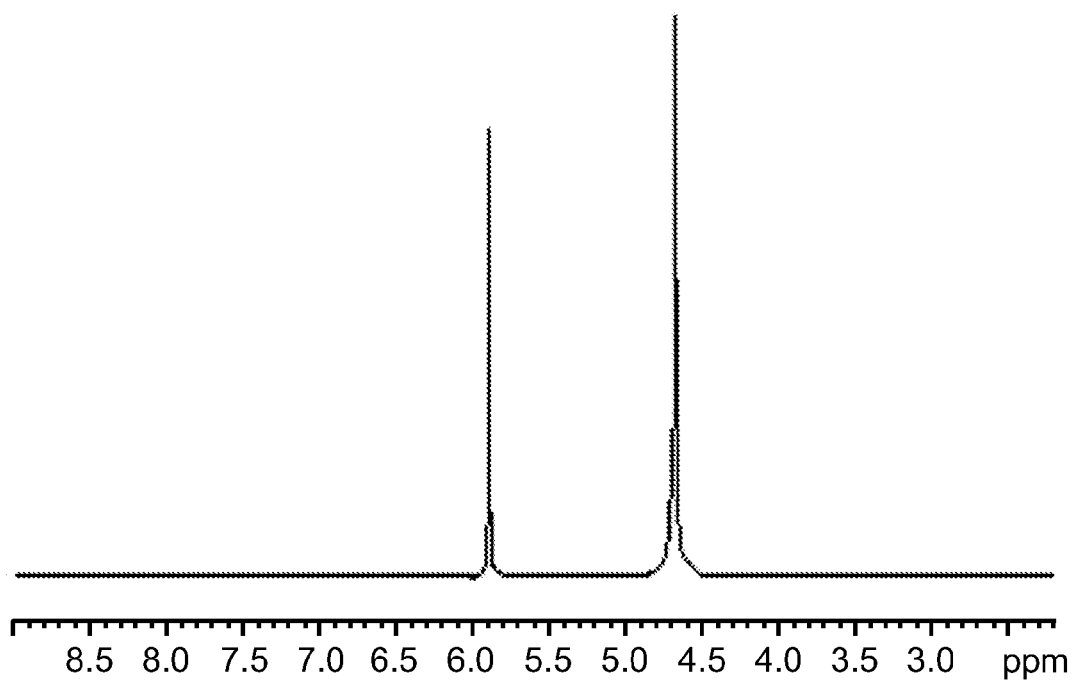
FIG. 5 shows the $^1$H NMR spectrum of a monomeric form of phloroglucinol.

Reference is again made to FIG. 1, which shows the chemical structure of monomeric phloroglucinol (1,3,5-trihydroxybenzene). FIG. 5 shows the $^1$H NMR spectrum of a monomeric form of phloroglucinol. As expected, it is clearly seen that only one type of proton is located in the aromatic zone of phloroglucinol. This corresponds to the -2, -4, and -6, positions of the protons, located in between the -1, -3, and -5, positions of the hydroxyl groups. It is also noticed that the presence of the hydroxyl groups caused a shift in the proton resonance to higher magnetic field (lower ppm value).

For attempting to identify the possible influence, if present, and extent thereof, that the oxidizer, in particular, $H_2O_2$, type of activating agent may have on the properties, characteristics, and behavior, of formulations of the adhesive composition of the present invention, two sample formulations of the adhesive composition were prepared and subjected to NMR measurements, and only the concentration of the $H_2O_2$ which functioned for 'activating' reaction (for example, polymerization, or/and cross-linking) of the phloroglucinol was varied, in particular, from 0.082 weight percent to 0.574 weight percent (of the total weight of the formulation). Except for these concentrations of $H_2O_2$, all other components of these two sample formulations were the same as those in the formulation indicated in Example 1, hereinbelow.

Figure 6:
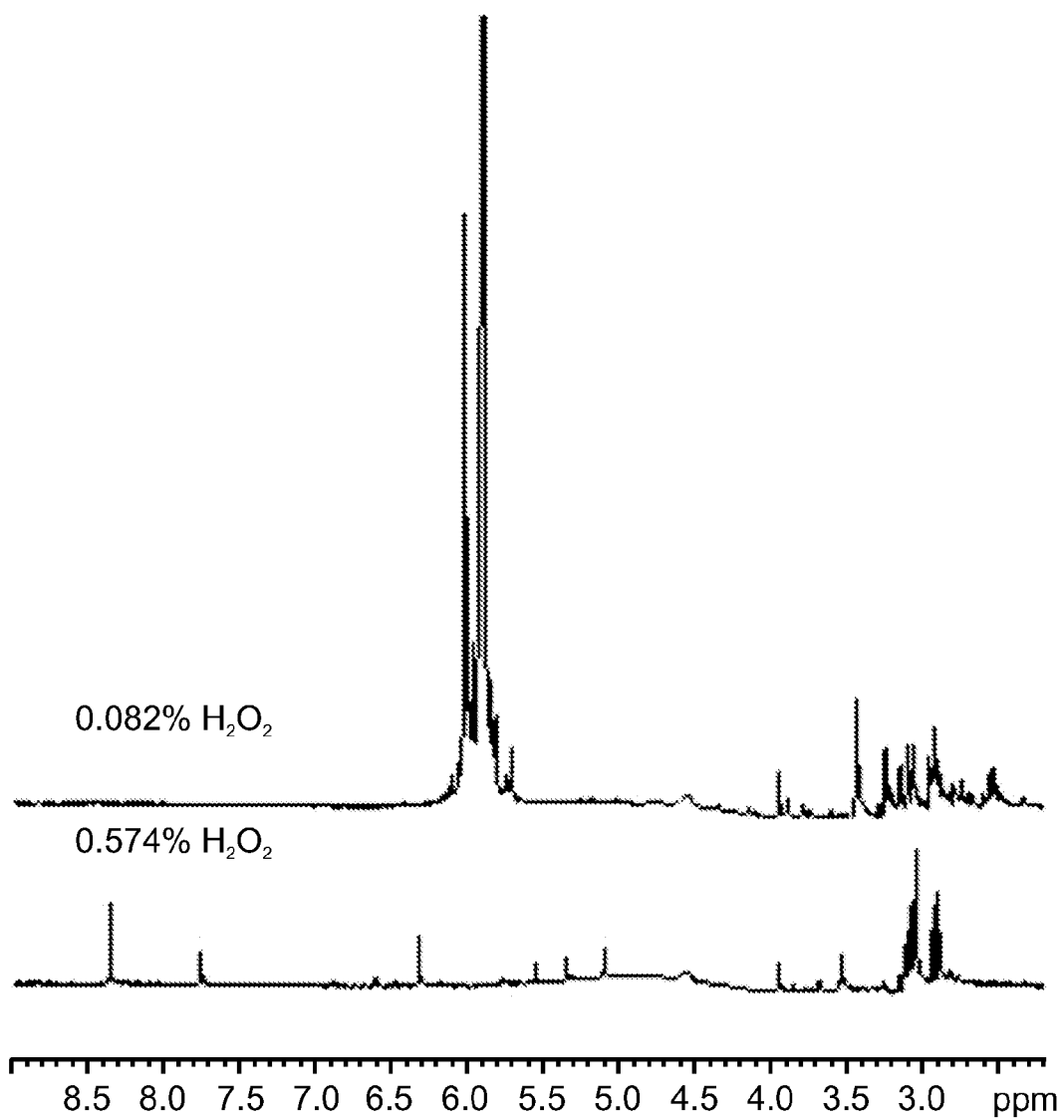
FIG. 6 comparatively shows the $^1$H NMR spectra of two sample formulations of the adhesive composition of the present invention, wherein the concentration of $H_2O_2$ was 0.082 weight percent and 0.574 weight percent, of the total weight of the formulation.

FIG. 6 shows the resulting $^1$H NMR spectra of the two sample formulations of the adhesive composition. Therein, it is clearly seen that for the sample adhesive formulation whose phloroglucinol activating concentration of $H_2O_2$ was 0.082 weight percent, the NMR spectrum includes a relatively strong signal at about 5.8 ppm. This result probably indicates the presence of the aromatic zone protons of the phloroglucinol monomer in the prepared adhesive formulation. By strong contrast, for the sample adhesive formulation whose phloroglucinol activating concentration of $H_2O_2$ was 0.574 weight percent, such a signal is completely absent from the NMR spectrum. This result probably indicates the absence of aromatic zone protons in the adhesive formulation.

Combining these results, and the indications thereof, leads to the mechanistic hypothesis that below a threshold value of the $H_2O_2$ concentration in the preparation of the adhesive formulation, most of the aromatic zone protons, of the phloroglucinol monomer remain intact, whereas above the threshold value of the $H_2O_2$ concentration, a radical coupling of the phloroglucinol aromatic rings to each other occurs, leading to the disappearance of the aromatic zone protons, of the phloroglucinol monomer.

Regardless of the actual reaction mechanism(s) taking place during formation of the adhesive composition of the present invention, the results of the NMR measurements clearly lead to the conclusion that, for the above tested samples of formulations of the adhesive composition, at least in the range of between 0.082 weight percent and 0.574 weight percent, varying the concentration of $H_2O_2$ as an oxidizer type of activating agent causes a change in the molecular structure of the adhesive composition of the present invention, in terms of the phloroglucinol being in a monomeric form, a polymeric form, or/and a cross-linked form.

Shear Type Adhesive Strength (Under Dry or Wet Conditions):

Shear type adhesive strength measurements were made on specimens of Mylar sandwiches or collagen sandwiches (under dry or wet conditions (surfaces)), which were prepared as described hereinabove, for determining the main characteristic property, that is, adhesive strength, of formulations of the adhesive composition of the present invention, under dry or wet conditions, for example, involving shear type adhesion of dry or wet surfaces.

Hereinbelow are ten examples wherein the shear type adhesive strength was measured using the Mylar or collagen sandwiches specimens, each including a different formulation of the adhesive composition. Examples 1-3 are of sandwich specimens having 'standard' adhesive formulations, wherein potassium iodide (KI) was included as the halogen salt type of activating agent in the preparation of the adhesive formulation. In Example 4, potassium bromide (KBr) replaced the potassium iodide as the halogen salt included in the preparation of the adhesive formulation.

For comparative purposes, for attempting to identify the possible influence, if present, and extent thereof, that an individual component may have on the properties, characteristics, and behavior, of the formulations of the adhesive composition of the present invention, for some samples of adhesive formulations which were subjected to shear type adhesive strength measurements, a selected individual component was omitted, or the concentration thereof was varied. In particular, in Examples 5-7, the haloperoxidase (in particular, bromoperoxidase (BPO)) type of activating agent was omitted from the indicated adhesive formulation, whereas, in Example 8, the water miscible polymer (in particular, sodium alginate) was omitted from the adhesive formulation. In Examples 9 and 10, the concentration of phloroglucinol in the adhesive formulations was significantly higher than that in the adhesive formulations of Examples 1-8.

Example 1

Shear Adhesive Strength

Specimen: Mylar sandwich; dry conditions (adhesion of dry surfaces).
Adhesive Formulation (with optional activating agents):
2.5 mg of phloroglucinol,
5 μl of bromoperoxidase (BPO) solution (1 ml of 0.0089 mg/ml (0.7 units/ml) in 1 ml water),
120 μl of hydrogen peroxide ($H_2O_2$) solution (0.5 ml of 30 percent solution in 8 ml water),
25 μl of potassium iodide (KI) solution (4.4 mg in 50 ml water),
12.5 mg of sodium alginate (Protanal LF 200 S; G content about 70 percent), and
5 μl of calcium chloride ($CaCl_2$) solution (10 ml of 1M solution in 90 ml water).
Shear adhesive strength: about 187 kPa.

Example 2

Shear Adhesive Strength

Specimen: Collagen sandwich; dry conditions (adhesion of dry surfaces).
Adhesive Formulation (with optional activating agents):
2.5 mg of phloroglucinol,
5 μl of bromoperoxidase (BPO) solution (1 ml of 0.0089 mg/ml (0.7 units/ml) in 1 ml water),
120 μl of hydrogen peroxide ($H_2O_2$) solution (0.5 ml of 30 percent solution in 8 ml water),
25 μl of potassium iodide (KI) solution (4.4 mg in 50 ml water),
12.5 mg of sodium alginate (Protanal LF 200 S; G content about 70 percent), and
5 μl of calcium chloride ($CaCl_2$) solution (10 ml of 1M solution in 90 ml water).
Shear adhesive strength: about 52 kPa.

Example 3

Shear Adhesive Strength

Specimen: Collagen sandwich; wet conditions (adhesion of wet surfaces).
Adhesive Formulation (with optional activating agents):
2.5 mg of phloroglucinol,
5 μl of bromoperoxidase (BPO) solution (1 ml of 0.0089 mg/ml (0.7 units/ml) in 1 ml water),
120 μl of hydrogen peroxide ($H_2O_2$) solution (0.5 ml of 30 percent solution in 8 ml water),
25 μl of potassium iodide (KI) solution (4.4 mg in 50 ml water),
12.5 mg of sodium alginate (Protanal LF 200 S; G content about 70 percent),
5 μl of calcium chloride ($CaCl_2$) solution (10 ml of 1M solution in 90 ml water), and
Shear adhesive strength: about 69 kPa.

Example 4

Shear Adhesive Strength

Specimen: Mylar sandwich; dry conditions (adhesion of dry surfaces).
Adhesive Formulation (with optional activating agents), (KBr instead of KI):
2.5 mg of phloroglucinol,
5 μl of bromoperoxidase (BPO) solution (1 ml of 0.0089 mg/ml (0.7 units/ml) in 1 ml water),
120 μl of hydrogen peroxide ($H_2O_2$) solution (0.5 ml of 30 percent solution in 8 ml water),
25 μl of potassium bromide (KBr) solution (4.4 mg in 50 ml water),
12.5 mg of sodium alginate (Protanal LF 200 S; G content about 70 percent), and
5 μl of calcium chloride ($CaCl_2$) solution (10 ml of 1M solution in 90 ml water).
Shear adhesive strength: about 21 kPa.

Example 5

Shear Adhesive Strength

Specimen: Mylar sandwich; dry conditions (adhesion of dry surfaces).
Adhesive Formulation (with optional activating agents), (without haloperoxidase (bromoperoxidase (BPO)):
2.5 mg of phloroglucinol,
120 μl of hydrogen peroxide ($H_2O_2$) solution (0.5 ml of 30 percent solution in 8 ml water),
25 μl of potassium iodide (KI) solution (4.4 mg in 50 ml water),
12.5 mg of sodium alginate (Protanal LF 200 S; G content about 70 percent), and
5 μl of calcium chloride ($CaCl_2$) solution (10 ml of 1M solution in 90 ml water).
Shear adhesive strength: about 187 kPa.

Example 6

Shear Adhesive Strength

Specimen: Collagen sandwich; dry conditions (adhesion of dry surfaces).
Adhesive Formulation (with optional activating agents), (without haloperoxidase (bromoperoxidase (BPO)):
2.5 mg of phloroglucinol,
120 µl of hydrogen peroxide ($H_2O_2$) solution (0.5 ml of 30 percent solution in 8 ml water),
25 µl of potassium iodide (KI) solution (4.4 mg in 50 ml water),
12.5 mg of sodium alginate (Protanal LF 200 S; G content about 70 percent), and
15 µl of calcium chloride ($CaCl_2$) solution (10 ml of 1M solution in 90 ml water).
Shear adhesive strength: about 113 kPa.

Example 7

Shear Adhesive Strength

Specimen: Collagen sandwich; wet conditions (adhesion of wet surfaces).
Adhesive Formulation (with optional activating agents), (without haloperoxidase (bromoperoxidase (BPO)):
2.5 mg of phloroglucinol,
120 µl of hydrogen peroxide ($H_2O_2$) solution (0.5 ml of 30 percent solution in 8 ml water),
25 µl of potassium iodide (KI) solution (4.4 mg in 50 ml water),
12.5 mg of sodium alginate (Protanal LF 200 S; G content about 70 percent), and
15 µl of calcium chloride ($CaCl_2$) solution (10 ml of 1M solution in 90 ml water).
Shear adhesive strength: about 49 kPa.

Example 8

Shear Adhesive Strength

Specimen: Mylar sandwich; dry conditions (adhesion of dry surfaces).
Adhesive Formulation (with optional activating agents), (without water miscible polymer (sodium alginate)):
2.5 mg of phloroglucinol,
5 µl of bromoperoxidase (BPO) solution (1 ml of 0.0089 mg/ml (0.7 units/ml) in 1 ml water),
120 µl of hydrogen peroxide ($H_2O_2$) solution (0.5 ml of 30 percent solution in 8 ml water),
25 µl of potassium iodide (KI) solution (4.4 mg in 50 ml water), and
5 µl of calcium chloride ($CaCl_2$) solution (10 ml of 1M solution in 90 ml water).
Shear adhesive strength: about 0.

Example 9

Shear Adhesive Strength

Specimen: Collagen sandwich; dry conditions (adhesion of dry surfaces).
Adhesive Formulation (with optional activating agents), (higher phloroglucinol concentration):
7.5 mg of phloroglucinol,
5 µl of bromoperoxidase (BPO) solution (1 ml of 0.0089 mg/ml (0.7 units/ml) in 1 ml water),
120 µl of hydrogen peroxide ($H_2O_2$) solution (0.5 ml of 30 percent solution in 8 ml water),
25 µl of potassium iodide (KI) solution (4.4 mg in 50 ml water),
12.5 mg of sodium alginate (Protanal LF 200 S; G content about 70 percent), and
5 µl of calcium chloride ($CaCl_2$) solution (10 ml of 1M solution in 90 ml water).
Shear adhesive strength: about 38 kPa.

Example 10

Shear Adhesive Strength

Specimen: Collagen sandwich; wet conditions (adhesion of wet surfaces).
Adhesive Formulation (with optional activating agents), (higher phloroglucinol concentration):
7.5 mg of phloroglucinol,
5 µl of bromoperoxidase (BPO) solution (1 ml of 0.0089 mg/ml (0.7 units/ml) in 1 ml water),
120 µl of hydrogen peroxide ($H_2O_2$) solution (0.5 ml of 30 percent solution in 8 ml water),
25 µl of potassium iodide (KI) solution (4.4 mg in 50 ml water),
12.5 mg of sodium alginate (Protanal LF 200 S; G content about 70 percent), and
5 µl of calcium chloride ($CaCl_2$) solution (10 ml of 1M solution in 90 ml water).
Shear adhesive strength: about 7 kPa.

Based on the results of the shear type adhesive strength measurements performed on the various formulations of the adhesive composition of the present invention, as described in Examples 1-10, hereinabove, following are selected notable comments and highlights. The following comments and highlights are relevant for the formulations of the adhesive composition tested at the above indicated conditions. Clearly, similar or different conclusions may be arrived at after testing similar formulations of the adhesive composition at different conditions, or after testing different formulations of the adhesive composition at similar conditions.

As shown by the results of Example 8, when the water miscible polymer, for example, in form of a salt of alginic acid, in particular, sodium alginate, is absent from the formulation of the composition of the present invention, the formulation exhibits essentially no adhesive strength. Accordingly, it can be concluded that, at least for the formulations and conditions of the composition tested hereinabove, a water miscible polymer needs to be present in the formulation of the composition of the present invention, in order for the formulation to exhibit adhesive strength. Apparently, by having the water miscible polymer in the formulation together with the phloroglucinol, the water miscible polymer reacts with the phloroglucinol in a manner which causes the combination to exhibit adhesive strength.

For collagen sandwich specimens, formulations of the adhesive composition of the present invention exhibit significant adhesive strength under either dry conditions (adhesion of dry collagen surfaces) or wet conditions (adhesion of wet collagen surfaces).

For Mylar and collagen sandwich specimens prepared in a similar manner, including same or similar formulations of the adhesive composition, the values of adhesive strength, under dry conditions, are typically greater for the Mylar sandwich specimens, compared to those of the collagen sandwich specimens. Accordingly, it can be concluded that such formulations of the adhesive composition of the present invention, under dry conditions, exhibit greater adhesive strength on the surfaces of the two Mylar strips compared to that exhibited on the surfaces of the two collagen films.

For Mylar sandwich specimens prepared in a similar manner, the formulation of the adhesive composition having been prepared with potassium iodide (KI) as the halogen salt type of activating agent (Example 1) yielded a significantly higher adhesive strength than the formulation of the adhesive composition having been prepared with potassium bromide (KBr) as the halogen salt type of activating agent (Example 4), namely, about 187 kPa compared to about 21 kPa, respectively.

Thus, based on, in addition to, or a consequence of, the above described aspects of novelty and inventiveness, the present invention as illustratively described and exemplified hereinabove, has several beneficial and advantageous aspects, characteristics, or features.

In particular, the present invention successfully overcomes disadvantages of using sutures, staples, or/and wires, in currently practiced tissue reattachment or repair procedures, and overcomes limitations associated with currently commercially available tissue adhesives made from synthetic or/and naturally existing components. The present invention also overcomes limitations associated with natural adhesive formulations made from marine or aquatic organisms, as well as overcoming limitations associated with biomimetic approximations of natural adhesives.

The present invention is safe and effective for use on (human or animal) subjects, and is especially applicable in the health care fields of medicine, dentistry, and veterinary science, for use by health care providers, such as medical, dental, and veterinary, surgeons, in procedures for reattaching or repairing body parts or components thereof, such as tissue, especially under wet conditions, for example, involving adhesion of wet surfaces. The present invention is commercially feasible and applicable, and doesn't require processing an enormous quantity of a marine or aquatic organism, followed by having to perform a relatively long sequence of various chemical and physical separation and purification processes and procedures, for producing a usable final form of the inventive adhesive. Additionally, the present invention is also generally applicable in a wide variety of other fields.

Tensile Type Adhesive Strength (Under Dry Conditions):

Tensile type adhesive strength measurements were made on specimens of Mylar sandwiches, collagen sandwiches, glass sandwiches, polystyrene sandwiches, or animal tissue (chicken breast) sandwiches, (under dry conditions (surfaces)), which were prepared as described hereinabove, for determining the main characteristic property, that is, tensile strength, of formulations of the adhesive composition of the present invention, under dry conditions, for example, involving tensile type adhesion (tension) of dry surfaces.

Hereinbelow are five examples, Examples 11-15, wherein tensile adhesive strength was measured using the Mylar, collagen, glass, polystyrene, or animal tissue (chicken breast), sandwich specimens, each including a different formulation of the adhesive composition.

Example 11

Tensile Adhesive Strength

Specimen: Mylar sandwich; dry conditions (adhesion of dry surfaces).
Adhesive Formulation (without optional activating agents):
2.5 mg of phloroglucinol,
12.5 mg of sodium alginate (Protanal LF 200 S; G content about 70 percent), and
5 μl of calcium chloride ($CaCl_2$) solution (10 ml of 1M solution in 90 ml water).
Tensile adhesive strength: 267 kPa.

Example 12

Tensile Adhesive Strength

Specimen: Mylar sandwich; dry conditions (adhesion of dry surfaces).
Adhesive Formulation (without optional activating agents):
5 mg of phloroglucinol,
12.5 mg of sodium alginate (Protanal LF 200 S; G content about 70 percent),
a volume of calcium carbonate ($CaCO_3$) suspension, 5 mM, and
a volume of glucono-b-lactone (GDL) solution, 10 mM.
Tensile adhesive strength: 131 kPa.

Example 13

Tensile Adhesive Strength

Specimen: Collagen sandwich; dry conditions (adhesion of dry surfaces).
Adhesive Formulation (without optional activating agents):
5 mg of phloroglucinol,
12.5 mg of sodium alginate (Protanal LF 200 S; G content about 70 percent),
a volume of calcium carbonate ($CaCO_3$) suspension, 7.5 mM, and
a volume of glucono-b-lactone (GDL) solution, 15 mM.
Tensile adhesive strength: 323 kPa.

Example 14

Tensile Adhesive Strength

Figure 7:
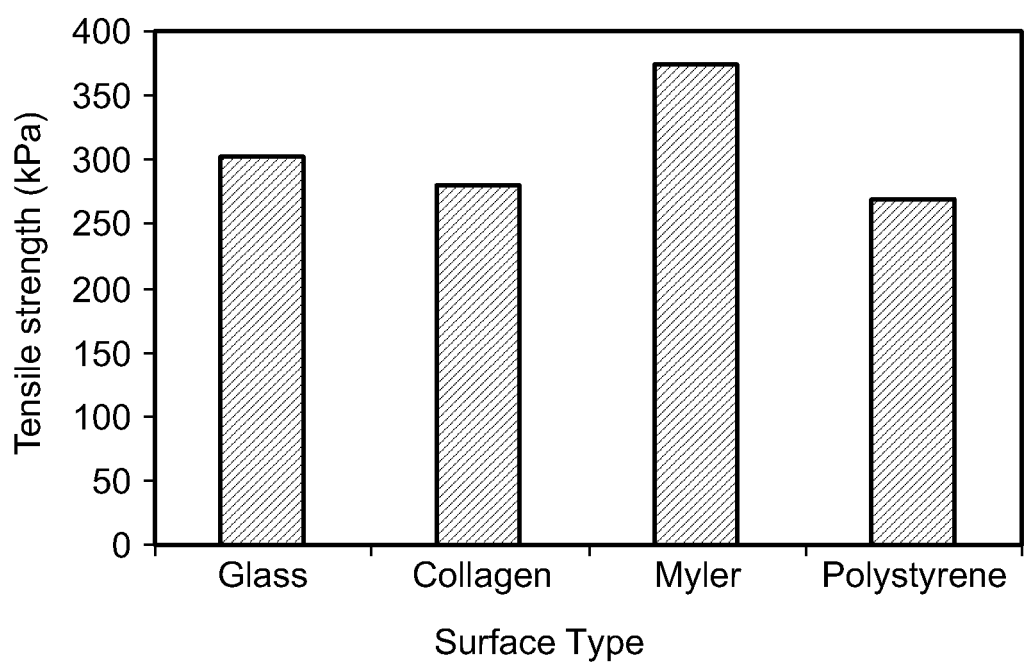
FIG. 7 is a graph of measured values of tensile strength (kPa) of an exemplary formulation of the adhesive composition of the present invention, for different types of surfaces, as detailed in Example 14, in accordance with the present invention.

Specimen: Mylar, Collagen, Glass, or, Polystyrene, sandwiches; dry conditions (adhesion of dry surfaces).
Adhesive Formulation (without optional activating agents):
5 mg of phloroglucinol,
15 mg of sodium alginate (Protanal LF 200 S; G content about 70 percent), and
10 μl of calcium chloride ($CaCl_2$) solution (10 ml of 1M solution in 90 ml water).
Tensile adhesive strength: As shown in FIG. 7.

Example 15

Tensile Adhesive Strength

Specimen: Animal tissue (chicken breast) sandwich; dry conditions (adhesion of dry surfaces).
Adhesive Formulation (without optional activating agents):
2.5 mg of phloroglucinol,
12.5 mg of sodium alginate (Protanal LF 200 S; G content about 70 percent), and
5 μl of calcium chloride ($CaCl_2$) solution (10 ml of 1M solution in 90 ml water).
Tensile adhesive strength: 153 kPa.

Based on the results of the tensile strength measurements performed on the various formulations of the adhesive composition of the present invention, as described in Examples 11-15, hereinabove, following are selected notable comments and highlights. The following comments and highlights are relevant for the formulations of the adhesive composition tested at the above indicated conditions. Clearly, similar or different conclusions may be arrived at after testing similar formulations of the adhesive composition at different conditions, or after testing different formulations of the adhesive composition at similar conditions.

As shown by the results of Examples 11-15, for a the different formulations of the adhesive composition, tensile strength is generally higher compared to shear adhesive strength. Moreover, as demonstrated in FIG. 7, the type of surface greatly effects the tensile strength. The results shown in Example 15 demonstrate good adhesion of the adhesive composition to animal tissue, thus suggesting the feasibility of utilizing the adhesive composition for medical applications.

It is appreciated that certain aspects and characteristics of the invention, which are, for clarity, described in the context of separate embodiments, may also be provided in combination in a single embodiment. Conversely, various aspects and characteristics of the invention, which are, for brevity, described in the context of a single embodiment, may also be provided separately or in any suitable sub-combination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

REFERENCES CITED BY NUMERALS

[1] Webster, I.; West, P. J., Adhesives for medical applications. In *Polymeric Biomaterials*; Dumitru. S., Ed.; Marcel Deker, New York, 2002, 703.
[2] McDermott, M. K.; Chen, T.; Williams, C. M.; Markley, K. M.; Payne, G. F., *Biomacromolecules* 2004, 5, 1270.
[3] Singer, A. J.; Thode, H. C., *The American Journal of Surgery* 2004, 187, 238.
[4] Lipatova, T. E., *Advances in Polymer Science* 1986, 79, 65.
[5] Reece, T. B.; Maxey, T. S.; Kron, I. L., *American Journal of Surgery* 2001, 182, 40S.
[6] Mo, X.; Iwata, H.; Matsuda, S.; Ikada, Y., *Journal of Biomaterials Science. Polymer edition* 2000, 11, 341.
[7] Ishihara, M.; Nakanishi, K.; Ono, K.; Sato, M.; Kikuchi, M.; Saito, Y.; Yura, H.; Matsui, T.; Hattori, H.; Uenoyama, M.; Kurita, A., *Biomaterials* 2001, 23, 833.
[8] White, J. K.; Titus, J. S.; Tanabe, H.; Aretz, H. T.; Torchiana, D. F., *Heart Surgery Forum* 2000, 3, 56.
[9] Ennker, I. C.; Ennker, J.; Schoon, D.; Schoon, H. A.; Rimpler, M.; Hetzer, R., *Annals of Thoracic Surgery* 1994, 57, 1622.
[10] Manabe, T.; Okino, H.; Tanaka, M.; Matsuda, T., *Biomaterials* 2004, 25, 5867.
[11] Masuda, T.; Fume, M.; Matsuda, T., *Tissue Engineering* 2004, 10, 523.
[12] Li, C.; Sajiki, T.; Nakayama, Y.; Fukui, M.; Matsuda, T., *Journal of Biomedical Materials Research, Part B: Applied Biomaterials* 2003, 66B, 439.
[13] Yu, M.; Deming, T. J., *Macromolecules* 1998, 31, 4739.
[14] Waite, J. H., *International Journal of Adhesion and Adhesives* 1987, 7, 9.
[15] Vreeland, V.; Grotkopp, E., *Research of Aqueous Water-resistant Phloroglucinol-type Adhesives And Glues Derived And Extracted From Algae And Activated By Oxidizing Agents*, University of California, USA.
[16] Vreeland, V.; Waite, J. H.; Epstein, L., *Journal of Phycology* 1998, 34, 1.
[17] U.S. Pat. No. 5,520,727, issued to Vreeland, et al., *Aqueous Algal-based Phenolic Type Adhesives And Glues*.
[18] Berglin, M.; Delage, L.; Potin, P.; Vilter, H.; Elwing, H., *Biomacromolecules* 2004, 5, 2376.
[19] Yamamoto, H.; Sakai, Y.; Ohkawa, K., *Biomacromolecules* 2000, 1, 543.
[20] Lee, B.; Dalsin, J.; P., M., *Biomacromolecules* 2002, 3, 1038.
[21] Huang, K.; Lee, B.; Messersmith, P. B., *Polymer Preprints (American Chemical Society, Division of Polymer Chemistry)* 2001, 42, 147.
[22] Lucas, J. M.; Vaccaro, E.; Waite, J. H., *Biopolymers* 2003, 8, 359.
[23] Ismailia, L.; Refouveleta, B.; Xiclunaa, A.; Roberta, J. F.; Guillaume, Y. C., *J. Pharm. Biomed. Anal.* 2003, 32, 549.
[24] Dumitriu, S., Polysaccharides as Biomaterials. In *Polymeric Biomaterials*; Dumitriu, S., Ed.; Marcel Dekker, Inc.: New York, 2002; 1.
[25] Draget, K. I., Ostgaad, K., and Smidrod, O., App. Microbiol. Biotechnol. 31, 79, 1989.

What is claimed is:

1. A method of manufacturing a composition-of-matter, wherein the composition-of-matter consists of a cross-linked form of a polysaccharide, at least one cross-linking agent comprised of divalent ions for effecting said cross-linked form of said polysaccharide, and at least one synthetically prepared phloroglucinol compound selected from group consisting of phloroglucinol, a derivative of phloroglucinol, and a polymer synthetically prepared from phloroglucinol or a derivative of phloroglucinol,
the method comprising:
providing the cross-linked form of the polysaccharide;
providing the at least one cross-linking agent comprised of divalent ions;
mixing the cross-linked form of the polysaccharide, the at least one cross-linking agent and the at least one phloroglucinol compound, thereby obtaining the composition-of-matter.

2. The method of claim 1, wherein the at least one phloroglucinol compound is in a monomeric form.

3. The method of claim 1, wherein the at least one phloroglucinol compound is in a non-cross-linked polymeric form or/and in a crosslinked polymeric form.

4. The method of claim 3, wherein said non-cross-linked polymeric form or/and said cross-linked polymeric form is an oligomer.

5. The method of claim 3, wherein the cross-linked polymeric form is obtained by admixing at least one activating agent with the cross-linked form of the polysaccharide and the at least one phloroglucinol compound, for effecting said crosslinked polymeric form.

6. The method of claim 5, wherein the at least one phloroglucinol compound is phloroglucinol or a derivative of phloroglucinol represented by the general structure:

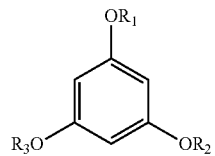

wherein:
R1-R3 are each independently selected from the group consisting of hydrogen, alkyl, cycloalkyl, and aryl.

7. The method of claim 1, wherein the at least one phloroglucinol compound is phloroglucinol.

8. The method of claim 1, wherein the at least one phloroglucinol compound is synthetically prepared.

9. The method of claim 1, wherein the at least one phloroglucinol compound is the polymer synthetically prepared from phloroglucinol or a derivative of phloroglucinol.

10. The method of claim 9, wherein the synthetically prepared polymer contains a plurality of from about 2 to about 500,000 phloroglucinol monomer units.

11. The method of claim 10, wherein the synthetically prepared polymer is an oligomer.

12. The method of claim 1, additionally including admixing with the cross-linked form of the polysaccharide and the at least one phloroglucinol compound at least one activating agent for effecting cross-linking of the at least one phloroglucinol compound.

13. The method of claim 12, wherein the at least one activating agent is selected from the group consisting of a haloperoxidase enzyme, an oxidizer, a halogen salt, and combinations thereof.

14. The method of claim 1, wherein said phloroglucinol compound has a concentration in a range of between about 0.01 weight percent and about 10 weight percent, of the total weight of the composition-of-matter.

15. The method claim 1, wherein the cross-linked form of the polysaccharide is a naturally existing, or synthetically prepared, form of a carbohydrate.

16. The method of claim 15, wherein the carbohydrate is selected from the group consisting of a salt form of alginic acid, alginic acid, and a combination thereof.

17. The method of claim 16, wherein the salt form of alginic acid or said alginic acid contains alpha-L-glucuronic acid (G) units in a range of between about 25 percent and about 75 percent.

18. The method of claim 14, wherein the carbohydrate is a salt form of alginic acid.

19. The method of claim 1, wherein said divalent ions are divalent calcium ions.

20. The method of claim 1, wherein the cross-linked form of the polysaccharide has a concentration in a range of between about 0.1 weight percent and about 10 weight percent, of the total weight of the composition-of-matter.

21. A method of adhering a first surface to a second surface, comprising applying a composition-of-matter consisting of a cross-linked form of a polysaccharide, at least one cross-linking agent comprised of divalent ions for effecting said cross-linked form of said polysaccharide, and at least one synthetically prepared pholorglucinol compound selected from the group consisting of phloroglucinol, a derivative of phloroglucinol, and a polymer synthetically prepared from phloroglucinol or a derivative of phloroglucinol,
   upon a designated area of the first surface, contacting said designated area with at least a portion of the second surface, and
   providing a sufficient period of time for the first surface to adhere to the second surface, thereby adhering the first surface to the second surface.

22. The method of claim 21, wherein each of the first surface and the second surface is dry.

23. The method of claim 21, performed under wet conditions wherein at least one of the first surface and the second surface is wet.

24. The method of claim 23, wherein at least one of the first surface and the second surface is a body part or a component thereof, of a human or animal subject.

25. The method of claim 24, wherein the component is a tissue.

* * * * *